(12) United States Patent
Green et al.

(10) Patent No.: US 6,670,399 B2
(45) Date of Patent: Dec. 30, 2003

(54) COMPOUNDS AND METHODS FOR MODULATING CEREBRAL AMYLOID ANGIOPATHY

(75) Inventors: Allan M. Green, Cambridge, MA (US); Francine Gervais, Ile Bizard (CA)

(73) Assignee: Neurochem (International) Limited (CH)

( * ) Notice: Subject to any disclaimer, the term of this patent is extended or adjusted under 35 U.S.C. 154(b) by 0 days.

(21) Appl. No.: 09/747,408

(22) Filed: Dec. 22, 2000

(65) Prior Publication Data

US 2003/0003141 A1 Jan. 2, 2003

Related U.S. Application Data

(60) Provisional application No. 60/171,877, filed on Dec. 23, 1999.

(51) Int. Cl.[7] ................ A61K 31/185; A61K 31/66; A61K 38/02; A61K 49/00
(52) U.S. Cl. ................ 514/578; 424/1.65; 424/9.1; 514/2; 514/114; 514/120; 514/126; 514/553
(58) Field of Search ................ 424/1.65, 1.69, 424/1.73, 1.77, 9.1, 78.17; 514/2, 23, 114, 120, 126, 553, 578; 562/30, 104

(56) References Cited

U.S. PATENT DOCUMENTS

| | | | |
|---|---|---|---|
| 4,386,081 A | 5/1983 | Helgstrand et al. | 424/212 |
| 4,540,564 A | 9/1985 | Bodor | 424/9 |
| 4,591,583 A | 5/1986 | Helgstrand et al. | 514/120 |
| 4,883,666 A | 11/1989 | Sabel et al. | 424/422 |
| 5,166,320 A | 11/1992 | Wu et al. | 530/395 |
| 5,194,654 A | 3/1993 | Hostetler et al. | 558/152 |
| 5,389,623 A | 2/1995 | Bodor | 514/169 |
| 5,455,044 A | 10/1995 | Kim et al. | 424/450 |
| 5,463,092 A | 10/1995 | Hostetler et al. | 554/40 |
| 5,576,018 A | 11/1996 | Kim et al. | 424/450 |
| 5,643,562 A | 7/1997 | Kisilevsky et al. | 424/78.31 |
| 5,728,375 A | 3/1998 | Kisilevsky et al. | 424/78.31 |
| 5,817,626 A * | 10/1998 | Findeis et al. | 514/12 |
| 5,840,294 A | 11/1998 | Kisilevsky et al. | 424/78.31 |
| 5,869,469 A | 2/1999 | Szarek et al. | 514/120 |
| 5,972,328 A | 10/1999 | Kisilevsky et al. | 424/78.31 |
| 6,114,175 A * | 9/2000 | Klunk et al. | 436/63 |

FOREIGN PATENT DOCUMENTS

| | | | |
|---|---|---|---|
| WO | WO 94/22437 | 10/1994 | |
| WO | WO 94/23697 | 10/1994 | |
| WO | WO 94/27602 | 12/1994 | |
| WO | WO 95/13796 | 5/1995 | |
| WO | 95/22963 | * 8/1995 | |
| WO | WO 96/07425 | 3/1996 | |
| WO | WO 96/10220 | 4/1996 | |
| WO | WO 96/28187 | 9/1996 | |
| WO | WO 96/39834 | 12/1996 | |
| WO | WO 97/03652 | 2/1997 | |
| WO | WO 98/22430 | 5/1998 | |
| WO | WO 98/22441 | 5/1998 | |
| WO | 98/25887 | * 6/1998 | |
| WO | 98/27972 | * 7/1998 | |
| WO | WO 99/08685 | 2/1999 | |
| WO | WO 99/40909 | 8/1999 | |
| WO | WO 99/59571 | 11/1999 | |
| WO | WO 99/62505 | 12/1999 | |
| WO | WO 00/31021 | 6/2000 | |
| WO | WO 00/68263 | 11/2000 | |

OTHER PUBLICATIONS

Mackic et al. Cerebrovascular Accumulation and Increased Blood–Brain Barrier . . . J. Neurochemistry. 1998, vol. 70, pp. 210–215.*

Barelli, H. et al., "Characterization of new polyclonal antibodies specific for 40 and 42 amino acid–long amyloid beta peptides; their use to examine the cell biology of presenilins and the immunohistochemistry of sporadic Alzheimer's disease and cerebral amyloid angiopathy cases," (1997) *Mol. Med.* Oct;3(10):695–707.

Berge et al. "Pharmaceutical Salts", (1977) *J. Pharm. Sci.* 66:1–19.

Deamer, et al., in *Liposomes*, Marcel Dekker, New York, (1983), 27.

Greenberg, "Cerebral amyloid angiopathy: prospects for clinical diagnosis and treatment," (1998) *Neurology*, 51:690–694.

Hileman, R. E. et al., "Glycosaminoglycan–protein interactions: definition of consensus sites in glycosaminoglycan binding proteins," (1998) *BioEssays* 20:156–167.

Hope, et al., "Generation of multilamellar and unilamellar phospholipid vesicles," (1986) *Chem. Phys. Lipids*, 40:89.

James, G. L. et al., "Benzodiazepine peptidomimetics: potent inhibitors of Ras farnesylation in animal cells," (1983) *Science* 260:1937–1942.

Kisilevsky, R. et al., "Arresting amyloidosis in vivo using small–molecule anionic sulphonates or sulphates: implications for Alzheimer's disease," (1995) *Nat. Med.* Feb; 1(2):143–8.

Lazorthes et al., "Advances in drug delivery systems and applications in neurosurgery," *Advances in Drug Delivery Systems and Applications in Neurosurgery*, 143–192 (Not dated).

Leveugle B. et al., "Heparin oligosaccharides that pass the blood–brainbarrier inhibit beta–amyloid precursor protein secretion and heparin binding to beta–amyloid peptide," (1998) *J. of Neurochem.* 70(2):736–744.

(List continued on next page.)

Primary Examiner—Jeffrey E. Russel
(74) Attorney, Agent, or Firm—Lahive & Cockfield, LLP; Elizabeth A. Hanley; Theodore R. West

(57) ABSTRACT

The invention provides methods of inhibiting cerebral amyloid angiopathy. The invention further provides methods of treating a disease state characterized by cerebral amyloid angiopathy in a subject with an Aβ40 inhibitor having the structure:

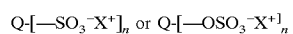

Q-[—SO$_3^-$X$^+$]$_n$ or Q-[—OSO$_3^-$X$^+$]$_n$ wherein Q is a carrier group; X+ is a cationic group; and n is one.

17 Claims, No Drawings

OTHER PUBLICATIONS

Mackic, J. et al., "Cerebrovascular accumulation and increased blood–brain barrier permeability to circulating Alzheimer's amyloid beta peptide in aged squirrel monkey with cerebral amyloid angiopathy," (1998) *J. Neurochem.* 70(1):210–5.

Nakamura, S. et al., "Histopathological studies of senile plaques and cerebral amyloidosis in cynomolgus monkeys," (1998) *J. Med. Primatol.* 27(5):244–52.

Ommaya et al., "Implantable devices for chronic access and drug delivery to the central nervous sysem," (1984) *Cancer Drug Delivery*, 1: 169–179.

Pillot et al., Specific modulation of the fusogenic properties of the Alzheimer beta–amyloid peptide by apolipoprotein E isoforms, (1997) *Eur. J. Biochem.* 243(3):650–9.

Silverman, R.B. *The Organic Chemistry of Drug Design and Drug Action*, Academic Press, Inc.:San Diego, CA, (1992), pp. 19–23.

Suzuki, N. et al., "High tissue content of soluble beta 1–40 is linked to cerebral amyloid angiopathy," (1994) *Am. J. Pathol.* 145(2):452–60.

Szoka, et al., "Comparative properties and methods of preparation of lipid vesicles (liposomes)," (1980) *Annual Reviews of Biophysics and Bioengineering*, 9:467.

*Physician's Desk Reference*, 51st Ed., pp. 541–545 (1997).

U.S. Provisional Application 60/130,464, Kisilevsky et al, filed Apr. 28, 1999.

* cited by examiner

SEQUENCE LISTING

```
<160> NUMBER OF SEQ ID NOS: 24

<210> SEQ ID NO 1
<211> LENGTH: 6
<212> TYPE: PRT
<213> ORGANISM: Homo sapiens

<400> SEQUENCE: 1

Lys Ile Val Phe Phe Ala
 1               5

<210> SEQ ID NO 2
<211> LENGTH: 7
<212> TYPE: PRT
<213> ORGANISM: Homo sapiens

<400> SEQUENCE: 2

Lys Lys Leu Val Phe Phe Ala
 1               5

<210> SEQ ID NO 3
<211> LENGTH: 6
<212> TYPE: PRT
<213> ORGANISM: Homo sapiens

<400> SEQUENCE: 3

Lys Leu Val Phe Phe Ala
```

```
                    1               5

<210> SEQ ID NO 4
<211> LENGTH: 6
<212> TYPE: PRT
<213> ORGANISM: Homo sapiens

<400> SEQUENCE: 4

Lys Phe Val Phe Phe Ala
 1               5

<210> SEQ ID NO 5
<211> LENGTH: 6
<212> TYPE: PRT
<213> ORGANISM: Homo sapiens

<400> SEQUENCE: 5

Ala Phe Phe Val Leu Lys
 1               5

<210> SEQ ID NO 6
<211> LENGTH: 4
<212> TYPE: PRT
<213> ORGANISM: Homo sapiens

<400> SEQUENCE: 6

Lys Leu Val Phe
 1

<210> SEQ ID NO 7
<211> LENGTH: 6
<212> TYPE: PRT
<213> ORGANISM: Homo sapiens

<400> SEQUENCE: 7

Lys Ala Val Phe Phe Ala
 1               5

<210> SEQ ID NO 8
<211> LENGTH: 5
<212> TYPE: PRT
<213> ORGANISM: Homo sapiens

<400> SEQUENCE: 8

Lys Leu Val Phe Phe
 1               5

<210> SEQ ID NO 9
<211> LENGTH: 6
<212> TYPE: PRT
<213> ORGANISM: Homo sapiens

<400> SEQUENCE: 9

Lys Val Val Phe Phe Ala
 1               5

<210> SEQ ID NO 10
<211> LENGTH: 6
<212> TYPE: PRT
<213> ORGANISM: Homo sapiens

<400> SEQUENCE: 10

Lys Ile Val Phe Phe Ala
 1               5
```

```
<210> SEQ ID NO 11
<211> LENGTH: 6
<212> TYPE: PRT
<213> ORGANISM: Homo sapiens

<400> SEQUENCE: 11

Lys Leu Val Phe Phe Ala
1               5

<210> SEQ ID NO 12
<211> LENGTH: 6
<212> TYPE: PRT
<213> ORGANISM: Homo sapiens

<400> SEQUENCE: 12

Lys Phe Val Phe Phe Ala
1               5

<210> SEQ ID NO 13
<211> LENGTH: 6
<212> TYPE: PRT
<213> ORGANISM: Homo sapiens

<400> SEQUENCE: 13

Ala Phe Phe Val Leu Lys
1               5

<210> SEQ ID NO 14
<211> LENGTH: 4
<212> TYPE: PRT
<213> ORGANISM: Homo sapiens

<400> SEQUENCE: 14

Lys Leu Val Phe
1

<210> SEQ ID NO 15
<211> LENGTH: 6
<212> TYPE: PRT
<213> ORGANISM: Homo sapiens

<400> SEQUENCE: 15

Lys Ala Val Phe Phe Ala
1               5

<210> SEQ ID NO 16
<211> LENGTH: 5
<212> TYPE: PRT
<213> ORGANISM: Homo sapiens

<400> SEQUENCE: 16

Lys Leu Val Phe Phe
1               5

<210> SEQ ID NO 17
<211> LENGTH: 6
<212> TYPE: PRT
<213> ORGANISM: Homo sapiens

<400> SEQUENCE: 17

Lys Val Val Phe Phe Ala
1               5

<210> SEQ ID NO 18
```

```
<211> LENGTH: 7
<212> TYPE: PRT
<213> ORGANISM: Homo sapiens

<400> SEQUENCE: 18

Lys Leu Val Phe Phe Ala Gln
 1               5

<210> SEQ ID NO 19
<211> LENGTH: 7
<212> TYPE: PRT
<213> ORGANISM: Homo sapiens

<400> SEQUENCE: 19

Lys Leu Val Phe Phe Ala Gln
 1               5

<210> SEQ ID NO 20
<211> LENGTH: 9
<212> TYPE: PRT
<213> ORGANISM: Homo sapiens

<400> SEQUENCE: 20

His His Gln Lys Leu Val Phe Phe Ala
 1               5

<210> SEQ ID NO 21
<211> LENGTH: 3
<212> TYPE: PRT
<213> ORGANISM: Homo sapiens

<400> SEQUENCE: 21

Asp Asp Asp
 1

<210> SEQ ID NO 22
<211> LENGTH: 6
<212> TYPE: PRT
<213> ORGANISM: Homo sapiens

<400> SEQUENCE: 22

Lys Val Asp Asp Gln Asp
 1               5

<210> SEQ ID NO 23
<211> LENGTH: 4
<212> TYPE: PRT
<213> ORGANISM: Homo sapiens

<400> SEQUENCE: 23

His His Gln Lys
 1

<210> SEQ ID NO 24
<211> LENGTH: 6
<212> TYPE: PRT
<213> ORGANISM: Homo sapiens

<400> SEQUENCE: 24

Gln Lys Leu Val Phe Phe
 1               5
```

COMPOUNDS AND METHODS FOR MODULATING CEREBRAL AMYLOID ANGIOPATHY

RELATED APPLICATIONS

This application claims the benefit of priority under 35 U.S.C. 119(e) to copending U.S. Provisional Application No. 60/171,877, filed Dec. 23, 1999, the entire contents of which are incorporated herein by reference.

BACKGROUND OF THE INVENTION

Cerebral amyloid angiopathy (CAA) remains a largely untreatable disease often not diagnosed until autopsy. It ranges in severity from asymptomatic amyloid deposition in otherwise normal cerebral vessels to complete replacement and breakdown of the cerebrovascular wall. Severe CAA can cause lobar cerebral hemorrhage, transient neurologic symptoms, and dementia with leukoencephalopathy. (see Greenberg, *Neurology* 1998, 51: 690–694).

Amyloid-β (Aβ) is a toxic peptide which is implicated in the pathogenesis of CAA. Aβ peptide is derived from a normal proteolytic cleavage of the precursor protein, the Amyloid-β precursor protein (βAPP). Advanced cases of CAA demonstrate structural changes to the walls of the amyloid-laden vessel such as cracking between layers, smooth muscle cell toxicity, microaneuryism formation, and fibrinoid necrosis.

The exact mechanisms involved in the genesis of cerebral amyloid angiopathy (CAA) have not been completely established, but it appears that a preponderance of the form of the 39-40 amino acid Aβ peptide (Aβ40) is responsible for the deposits on blood vessel wall cells which lead to CAA, in comparison to the 42-43 amino acid Aβ peptides (Aβ42 and Aβ43), which are implicated in other amyloid-related conditions such as Alzheimer's Disease (AD).

SUMMARY OF THE INVENTION

The present invention provides methods for modulating, e.g., inhibiting and/or preventing, cerebral amyloid angiopathy. The present invention is based, at least in part, on the discovery that compounds which interfere with the deposition of Aβ peptide, e.g., the Aβ40 peptide, in blood vessel wall cells, prevent the structural changes to cerebral blood vessels like capillaries, that lead to CAA. It is believed, without intending to limit the invention as claimed herein, that the compounds of the invention interfere with the association of the Aβ40 peptide, e.g., the association of the Aβ40 peptide to the sulfate GAGs present at the smooth muscle cell surface, and thus prevent intracellular and extracellular amyloid deposition. However, while it is believed that inhibition of Aβ40 is a significant factor in inhibiting CAA, the Aβ40 inhibitors of the invention may well work in other ways to inhibit or prevent CAA, and these are intended to be part of the present invention.

Accordingly, this invention pertains to a method of modulating, e.g., inhibiting and/or preventing, cerebral amyloid angiopathy. The method includes contacting a blood vessel wall cell with an Aβ40 inhibitor, such that the compound inhibits or prevents cerebral amyloid angiopathy. The Aβ40 inhibitor is believed to at least interfere with the ability of the Aβ40 peptide to form amyloid fibrils and/or with the ability of the Aβ40 peptide to bind to a cell (e.g., blood vessel wall smooth muscle cells, pericytes or endothelial cells) surface molecule or structure, forming deposits on the walls of the blood vessel and thus prevent Aβ-induced cell death and/or the structural changes to cerebral blood vessels, e.g., capillaries, medium sized arteries, or arterioles, that lead to CAA. The Aβ40 peptide can be either in a soluble form or in a fibril form.

In one embodiment, the Aβ40 inhibitor may be ethanesulfonic acid, 1,2-ethanedisulfonic acid, 1-propanesulfonic acid, 1,3-propanedisulfonic acid, 1,4-butanedisulfonic acid, 1,5-pentanedisulfonic acid, 2-aminoethanesulfonic acid, or 4-hydroxy-1-butanesulfonic acid, and pharmaceutically acceptable salts thereof. In other preferred embodiments, the Aβ40 inhibitor may be 1-butanesulfonic acid, 1-decanesulfonic acid, 2-propanesulfonic acid, 3-pentanesulfonic acid, or 4-heptanesulfonic acid, and pharmaceutically acceptable salts thereof. In yet further preferred embodiments, the Aβ40 inhibitor may be 1,7-dihydroxy-4-heptanesulfonic acid, 3-amino-1-propanesulfonic acid, or a pharmaceutically acceptable salt thereof. In another embodiment the Aβ40 inhibitor is a peptide or a peptidomimetic which interacts with specific regions of the Aβ peptide such as the regions responsible for cellular adherence (aa 10-16), GAG binding site region (13-16) or the region responsible for the β-sheet formation (16-21). These peptides are the d-stereoisomers of the Aβ or complementary image of the Aβ peptide.

In one embodiment, the Aβ40 inhibitor is administered in a pharmaceutically acceptable formulation. The pharmaceutically acceptable formulation can be a dispersion system like a lipid-based formulation, a liposome formulation, or a multivesicular liposome formulation. The pharmaceutically acceptable formulation can also comprise a polymeric matrix, e.g., synthetic polymers such as polyesters (PLA, PLGA), polyethylene glycol, poloxomers, polyanhydrides, and pluronics; or naturally derived polymers, such as albumin, alginate, cellulose derivatives, collagen, fibrin, gelatin, and polysaccharides. In other preferred embodiments, the pharmaceutically acceptable formulation provides sustained delivery of the Aβ40 inhibitor to the target site.

Yet another aspect of the invention pertains to a method of treating a disease state characterized by cerebral amyloid angiopathy in a subject. The method includes administering an Aβ40 inhibitor to the subject, such that the disease state characterized by cerebral amyloid angiopathy is treated, e.g., inhibited or prevented.

Another aspect of the invention pertains to a method of modulating, e.g., inhibiting and/or preventing, cerebral amyloid angiopathy, including contacting a blood vessel wall cell with an Aβ40 inhibitor having the structure:

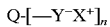

$$Q\text{-}[\text{---}Y^-X^+]_n$$

wherein $Y^-$ is an anionic group at physiological pH; Q is a carrier group; $X^+$ is a cationic group; and n is an integer selected such that the biodistribution of the Aβ40 inhibitor for an intended target site is not prevented while maintaining activity of the Aβ40 inhibitor, provided that the Aβ40 inhibitor is not chondroitin sulfate A, such that cerebral amyloid angiopathy is inhibited or prevented.

In yet another aspect, the invention features a method of modulating, e.g., inhibiting and/or preventing, cerebral amyloid angiopathy, including contacting a blood vessel wall cell with an Aβ40 inhibitor having the structure:

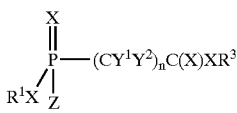

wherein Z is $XR^2$ or $R^4$, $R^1$ and $R^2$ are each independently hydrogen, a substituted or unsubstituted aliphatic group (preferably a branched or straight-chain aliphatic moiety having from 1 to 24 carbon atoms in the chain; or an unsubstituted or substituted cyclic aliphatic moiety having from 4 to 7 carbon atoms in the aliphatic ring; preferred aliphatic and cyclic aliphatic groups are alkyl groups, more preferably lower alkyl), an aryl group, a heterocyclic group, or a salt-forming cation; $R^3$ is hydrogen, lower alkyl, aryl, or a salt-forming cation; $R^4$ is hydrogen, lower alkyl, aryl or amino (including alkylamino, dialkylamino (including cyclic amino moieties), arylamino, diarylamino, and alkylarylamino); X is, independently for each occurrence, O or S; $Y^1$ and $Y^2$ are each independently hydrogen, halogen (e.g., F, Cl, Br, or I), alkyl (preferably lower alkyl), amino, hydroxy, alkoxy, or aryloxy; and n is an integer from 0 to 12 (more preferably 0 to 6, more preferably 0 or 1), such that cerebral amyloid angiopathy is inhibited or prevented.

Other features and advantages of the invention will be apparent from the following detailed description, and from the claims.

DETAILED DESCRIPTION OF THE INVENTION

The present invention is based, at least in part, on the discovery that compounds which interfere with the ability of the Aβ40 peptide to form deposits in cerebral blood vessels, e.g., on the smooth muscle cells thereof, and thus prevent the structural changes to cerebral blood vessels that lead to CAA.

As used herein, the language "contacting" is intended to include both in vivo, in vitro, or ex vivo methods of bringing an Aβ40 inhibitor into proximity with a blood vessel wall cell, such that the Aβ40 inhibitor can inhibit or prevent CAA, e.g., via inhibiting the deposition of the Aβ40 peptide. For example, the blood vessel wall cell can be contacted with an Aβ40 inhibitor in vivo by administering the Aβ40 inhibitor to a subject either parenterally, e.g., intravenously, intradermally, subcutaneously, orally (e.g., via inhalation), transdermally (topically), transmucosally, or rectally. A blood vessel wall cell can also be contacted in vitro by, for example, adding an Aβ40 inhibitor into a tissue culture dish in which blood vessel wall smooth muscle cells are grown.

As used herein, the term "subject" is intended to include animals susceptible to states characterized by cerebral amyloid angiopathy, preferably mammals, most preferably humans. In a preferred embodiment, the subject is a primate. In an even more preferred embodiment, the primate is a human. Other examples of subjects include experimental animals such as mice, rats, dogs, cats, goats, sheep, pigs, and cows. The experimental animal can be an animal model for a disorder, e.g., a transgenic mouse.

The term "blood vessel wall cell" includes smooth muscle cells, pericytes and endothelial cells. In a preferred embodiment the blood vessel wall cell is a smooth muscle cell.

Aβ40 Inhibitors

In one embodiment, the method of the invention includes contacting a blood vessel wall cell in vitro or administering to a subject in vivo, an effective amount of an Aβ40 inhibitor, which has at least one anionic group covalently attached to a carrier molecule. As used herein, an "Aβ40 inhibitor" includes compounds which can interfere with the ability of a CAA-associated Aβ peptide, e.g., Aβ40, to either form fibrils or interact with a cell surface molecule such as a proteoglycan constituent of a basement membrane, e.g., a glycosaminoglycan. An Aβ40 inhibitor can interfere with the ability of both fibrillar or non-fibrillar CAA-associated Aβ peptide, e.g., Aβ40, to interact with a cell surface molecule.

The Aβ40 inhibitor can have the structure:

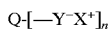

wherein $Y^-$ is an anionic group at physiological pH; Q is a carrier group; $X^+$ is a cationic group; and n is an integer. The number of anionic groups ("n") is selected such that the biodistribution of the Aβ40 inhibitor for an intended target site is not prevented while maintaining activity of the Aβ40 inhibitor. For example, the number of anionic groups is not so great as to prevent traversal of an anatomical barrier, such as a cell membrane, or entry across a physiological barrier, such as the blood-brain barrier. In one embodiment, n is an integer between 1 and 10. In another embodiment, n is an integer between 3 and 8. These compounds are described in U.S. Pat. Nos. 5,643,562, 5,972,328, 5,728,375, 5,840,294, and U.S. application Ser. No. 60/131,464. Such compounds also include or can be described as glycosaminoglycan ("GAG") mimics or mimetics. Other compounds which may be included are those described in, e.g., Pillot et al., *Eur. J. Biochem* vol. 243 No. 3, 1997 (apoE2, apoE3); WO98/22441; WO98/22430; WO96/10220; WO96/07425; and WO96/39834.

An anionic group of an Aβ40 inhibitor of the invention is a negatively charged moiety that, when attached to a carrier group, can interfere with the ability of a CAA-associated Aβ peptide, e.g., Aβ40, to either form fibrils or interact with a cell surface molecule such as a proteoglycan constituent of a basement membrane, e.g., a glycosaminoglycan ("GAG"). As such, Aβ40 is inhibited from forming deposits in blood vessels, e.g., cerebral blood vessel wall smooth muscle cells, thus preventing hardening of the vessel walls and, therefore, cerebral amyloid angiopathy.

For purposes of this invention, the anionic group is negatively charged at physiological pH. Preferably, the anionic Aβ40 inhibitor mimics the structure of a sulfated proteoglycan, i.e., is a sulfated compound or a functional equivalent thereof. "Functional equivalents" of sulfates are intended to include compounds such as sulfamates as well as bioisosteres. Bioisosteres encompass both classical bioisosteric equivalents and non-classical bioisosteric equivalents. Classical and non-classical bioisosteres of sulfate groups are known in the art (see e.g., Silverman, R. B. *The Organic Chemistry of Drug Design and Drug Action*, Academic Press, Inc.: San Diego, Calif., 1992, pp.19–23). Accordingly, an Aβ40 inhibitor of the invention can comprise at least one anionic group including sulfonates, sulfates, sulfamates, phosphonates, phosphates, carboxylates, and heterocyclic groups of the following formulae:

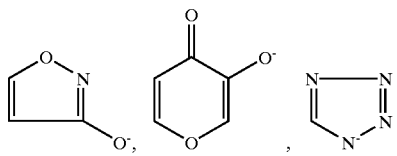

Depending on the carrier group, more than one anionic group can be attached thereto. When more than one anionic group is attached to a carrier group, the multiple anionic groups can be the same structural group (e.g., all sulfonates) or, alternatively, a combination of different anionic groups can be used (e.g., sulfonates, phosphonates, and sulfates, etc.).

The ability of an Aβ40 inhibitor of the invention to inhibit an interaction between Aβ40 peptide and a glycoprotein or proteoglycan constituent of a basement membrane can be assessed by an in vitro binding assay, such as the one described in Leveugle B. et al. (1998) *J. of Neurochem.* 70 (2): 736–744. Briefly, a constituent of the basement membrane, preferably a glycosaminoglycan (GAG) can be radiolabeled, e.g., at a specific activity of 10,000 cpm, and then incubated with Aβ40 peptide-Sepharose beads at, for example, a ratio of 5:1 (v/v) in the presence or absence of the Aβ40 inhibitor. The Aβ40 peptide-Sepharose beads and the radiolabeled GAG can be incubated for approximately 30 minutes at room temperature and then the beads can be successively washed with a Tris buffer solution containing NaCl (0.55 M and 2 M). The binding of the basement membrane constituent (e.g., GAG) to the Aβ40 peptide can then be measured by collecting the fractions from the washings and subjecting them to scintillation counting. An Aβ40 inhibitor which inhibits an interaction between Aβ40 and a glycoprotein or proteoglycan constituent of a basement membrane, e.g., GAG, will increase the amount of radioactivity detected in the washings.

In the same manner, the invention relates to a method of diagnosing CAA in vivo, whereas an labeled inhibitor of the invention is administered to a subject and the disposition of the inhibitor is determined to see whether a CAA-related condition exists. The label may be one conventionally known in the art which allows for detection of the compound either in vivo or in vitro, e.g., radiolabel, fluorescent, etc. Using techniques with which those of ordinary skill in the art will be familiar, e.g., PET scan, bound tagged inhibitor of the invention may be visualized, e.g., in regions where CAA would be found, such as near the cerebellum.

Preferably, an Aβ40 inhibitor of the invention interacts with a binding site for a basement membrane glycoprotein or proteoglycan in Aβ40 and thereby inhibits the binding of the Aβ40 peptide to the basement membrane constituent, e.g., GAG. Basement membrane glycoproteins and proteoglycans include GAG, laminin, collagen type IV, fibronectin, chondroitin sulfate, perlecan, and heparan sulfate proteoglycan (HSPG). In a preferred embodiment, the therapeutic compound inhibits an interaction between an Aβ40 peptide and a GAG. Consensus binding site motifs for GAG in amyloidogenic proteins have been described (see, for example, Hileman R. E. et al. (1998) *BioEssays* 20: 156–167). For example, a GAG consensus binding motif can be of the general formula X-B-B-X-B-X or X-B-B-B-X-X-B-X, wherein B are basic amino acids (e.g., lysine or arginine) and X are hydropathic amino acids. A GAG consensus binding motif can further be of the general formula T-X-X-B-X-X-T-B-X-X-X-T-B-B, wherein T defines a turn of a basic amino acid, Bs are basic amino acids (e.g., lysine, arginine, or occasionally glutamine) and X are hydropathic amino acids. The distance between the first and the second turn can range from approximately 12 Å to 17 Å. The distance between the second and the third turn can be approximately 14 Å. The distance between the first and the third turn can range from approximately 13 Å to 18 Å.

Accordingly, in the Aβ40 inhibitors of the invention, when multiple anionic groups are attached to a carrier group, the relative spacing of the anionic groups can be chosen such that the anionic groups (e.g., sulfonates or phosphonates) optimally interact with the basic residues within the GAG binding site (thereby inhibiting interaction of GAG with the site). For example, anionic groups can be spaced approximately 15±1.5 Å, 14±1.5 Å and/or 16±1.5 Å apart, or appropriate multiples thereof, such that the relative spacing of the anionic groups allows for optimal interaction with a binding site for a basement membrane constituent (e.g., GAG) in an Aβ40 peptide.

Aβ40 inhibitors of the invention typically further comprise a counter cation (i.e., $X^+$ in the general formula: $Q\text{-}[\text{-}Y^-X^+]_n$). Cationic groups include positively charged atoms and moieties. If the cationic group is hydrogen, $H^+$, then the compound is considered an acid, e.g., ethanesulfonic acid. If hydrogen is replaced by a metal or its equivalent, the compound is a salt of the acid. Pharmaceutically acceptable salts of the Aβ40 inhibitor are within the scope of the invention. For example, $X^+$ can be a pharmaceutically acceptable alkali metal, alkaline earth, higher valency cation, polycationic counter ion or ammonium. A preferred pharmaceutically acceptable salt is a sodium salt but other salts are also contemplated within their pharmaceutically acceptable range.

Within the Aβ40 inhibitor, the anionic group(s) is covalently attached to a carrier group. Suitable carrier groups include aliphatic groups, alicyclic groups, heterocyclic groups, aromatic groups, and groups derived from carbohydrates, polymers, peptides, peptide derivatives, or combinations thereof. A carrier group can be substituted, e.g., with one or more amino, nitro, halogen, thiol or hydroxyl groups.

As used herein, the term "carbohydrate" is intended to include substituted and unsubstituted mono-, oligo-, and polysaccharides. Monosaccharides are simple sugars usually of the formula $C_6H_{12}O_6$ that can be combined to form oligosaccharides or polysaccharides. Monosaccharides include enantiomers and both the D and L stereoisomers of monosaccharides. Carbohydrates can have multiple anionic groups attached to each monosaccharide moiety. For example, in sucrose octasulfate, four sulfate groups are attached to each of the two monosaccharide moieties.

As used herein, the term "polymer" is intended to include molecules formed by the chemical union of two or more combining subunits called monomers. Monomers are molecules or compounds which usually contain carbon and are of relatively low molecular weight and simple structure. A monomer can be converted to a polymer by combination with itself or other similar molecules or compounds. A polymer may be composed of a single identical repeating subunit or multiple different repeating subunits (copolymers). Polymers within the scope of this invention include substituted and unsubstituted vinyl, acryl, styrene and carbohydrate-derived polymers and copolymers and salts thereof. In one embodiment, the polymer has a molecular weight of approximately 800–1000 Daltons. Examples of polymers with suitable covalently attached anionic groups (e.g., sulfonates or sulfates) include poly(2-acrylamido-2-methyl-1-propanesulfonic acid); poly(2-acrylamido-2-methyl-1-propanesulfonic acid-co-acrylonitrile); poly(2-acrylamido-2-methyl-1-propanesulfonic acid-co-styrene); poly(vinylsulfonic acid); poly(sodium 4-styrenesulfonic acid); and sulfates and/or sulfonates derived from: poly (acrylic acid); poly(methyl acrylate); poly(methyl methacrylate); and poly(vinyl alcohol); and pharmaceutically acceptable salts thereof. Examples of polymers with suitable covalently attached anionic groups include those of the formula:

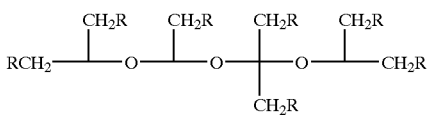

wherein R is SO₃H or OSO₃H; and pharmaceutically acceptable salts thereof.

Peptides and peptide derivatives can also act as carriers. The term "peptide" includes two or more amino acids covalently attached through a peptide bond. Amino acids which can be used in peptide carriers include those naturally occurring amino acids found in proteins such as glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan. The term "amino acid" further includes analogs, derivatives and congeners of naturally occurring amino acids, one or more of which can be present in a peptide derivative. For example, amino acid analogs can have lengthened or shortened side chains or variant side chains with appropriate functional groups. Also included are the D and L stereoisomers of an amino acid when the structure of the amino acid admits of stereoisomeric forms. The term "peptide derivative" further includes compounds which contain molecules which mimic a peptide backbone but are not amino acids (so-called peptidomimetics), such as benzodiazepine molecules (see e.g., James, G. L. et al. (1993) *Science* 260: 1937–1942). The anionic groups can be attached to a peptide or peptide derivative through a functional group on the side chain of certain amino acids or other suitable functional group. For example, a sulfate group can be attached through the hydroxyl side chain of a serine residue. A peptide can be designed to interact with a binding site for a basement membrane constituent (e.g., a GAG) in an Aβ40 peptide (as described above). Accordingly, in one embodiment, the peptide comprises four amino acids and anionic groups (e.g., sulfonates) are attached to the first, second and fourth amino acid. For example, the peptide can be Ser-Ser-Y-Ser, wherein an anionic group is attached to the side chain of each serine residue and Y is any amino acid. In addition to peptides and peptide derivatives, single amino acids can be used as carriers in the Aβ40 inhibitor of the invention. For example, cysteic acid, the sulfonate derivative of cysteine, can be used. Peptides such as disclosed in International Application No. WO 00/68263 may be used, also, e.g., Lys-Ile-Val-Phe-Phe-Ala (SEQ ID NO: 1); Lys-Lys-Leu-Val-Phe-Phe-Ala (SEQ ID NO: 2); Lys-Leu-Val-Phe-Phe-Ala (SEQ ID NO: 3); Lys-Phe-Val-Phe-Phe-Ala (SEQ ID NO: 4); Ala-Phe-Phe-Val-Leu-Lys (SEQ ID NO: 5); Lys-Leu-Val-Phe (SEQ ID NO: 6); Lys-Ala-Val-Phe-Phe-Ala (SEQ ID NO: 7); Lys-Leu-Val-Phe-Phe (SEQ ID NO: 8); Lys-Val-Val-Phe-Phe-Ala (SEQ ID NO: 9); Lys-Ile-Val-Phe-Phe-Ala-NH, (SEQ ID NO: 10); Lys-Leu-Val-Phe-Phe-Ala-NH, (SEQ ID NO: 11); Lys-Phe-Val-Phe-Phe-Ala-NH, (SEQ ID NO: 12); Ala-Phe-Phe-Val-Leu-Lys-NH₂ (SEQ ID NO: 13); Lys-Leu-Val-Phe-NH₂ (SEQ ID NO: 14); Lys-Ala-Val-Phe-Phe-Ala-NH₂ (SEQ ID NO: 15); Lys-Leu-Val-Phe-Phe-NH₂ (SEQ ID NO: 16); Lys-Val-Val-Phe-Phe-Ala-NH₂ (SEQ ID NO: 17); Lys-Leu-Val-Phe-Phe-Ala-Gln (SEQ ID NO: 18); Lys-Leu-Val-Phe-Phe-Ala-Gln-NH₂ (SEQ ID NO: 19); His-His-Gln-Lys-Leu-Val-Phe-Phe-Ala-NH₂ (SEQ ID NO: 20); Asp-Asp-Asp (SEQ ID NO: 21); Lys-Val-Asp-Asp-Gln-Asp (SEQ ID NO: 22); His-His-Gln-Lys (SEQ ID NO: 23); and Gln-Lys-Leu-Val-Phe-NH₂ (SEQ ID NO: 24).

The term "aliphatic group" is intended to include organic compounds characterized by straight or branched chains, typically having between 1 and 22 carbon atoms. Aliphatic groups include alkyl groups, alkenyl groups and alkynyl groups. In complex structures, the chains can be branched or cross-linked. Alkyl groups include saturated hydrocarbons having one or more carbon atoms, including straight-chain alkyl groups and branched-chain alkyl groups. Such hydrocarbon moieties may be substituted on one or more carbons with, for example, a halogen, a hydroxyl, a thiol, an amino, an alkoxy, an alkylcarboxy, an alkylthio, or a nitro group. Unless the number of carbons is otherwise specified, "lower aliphatic" as used herein means an aliphatic group, as defined above (e.g., lower alkyl, lower alkenyl, lower alkynyl), but having from one to six carbon atoms. Representatives of such lower aliphatic groups, e.g., lower alkyl groups, are methyl, ethyl, n-propyl, isopropyl, 2-chloropropyl, n-butyl, sec-butyl, 2-aminobutyl, isobutyl, tert-butyl, 3-thiopentyl, and the like. As used herein, the term "amino" means —NH₂; the term "nitro" means —NO₂; the term "halogen" designates —F, —Cl, —Br or —I; the term "thiol" means SH; and the term "hydroxyl" means —OH. Thus, the term "alkylamino" as used herein means —NHR wherein R is an alkyl group as defined above. The term "alkylthio" refers to —SR, wherein R is an alkyl group as defined above. The term "alkylcarboxyl" as used herein means —COOR, wherein R is an alkyl group as defined above. The term "alkoxy" as used herein means —OR, wherein R is an alkyl group as defined above. Representative alkoxy groups include methoxy, ethoxy, propoxy, tert-butoxy and the like. The terms "alkenyl" and "alkynyl" refer to unsaturated aliphatic groups analogous to alkyls, but which contain at least one double or triple bond respectively.

The term "alicyclic group" is intended to include closed ring structures of three or more carbon atoms. Alicyclic groups include cycloparaffins or naphthenes which are saturated cyclic hydrocarbons, cycloolefins which are unsaturated with two or more double bonds, and cycloacetylenes which have a triple bond. They do not include aromatic groups. Examples of cycloparaffins include cyclopropane, cyclohexane, and cyclopentane. Examples of cycloolefins include cyclopentadiene and cyclooctatetraene. Alicyclic groups also include fused ring structures and substituted alicyclic groups such as alkyl substituted alicyclic groups. In the instance of the alicyclics such substituents can further comprise a lower alkyl, a lower alkenyl, a lower alkoxy, a lower alkylthio, a lower alkylamino, a lower alkylcarboxyl, a nitro, a hydroxyl, —CF₃, —CN, or the like.

The term "heterocyclic group" is intended to include closed ring structures in which one or more of the atoms in the ring is an element other than carbon, for example, nitrogen, or oxygen. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —CF₃, —CN, or the like.

The term "aromatic group" is intended to include unsaturated cyclic hydrocarbons containing one or more rings. Aromatic groups include 5- and 6-membered single-ring groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. The aromatic ring may be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —CF$_3$, —CN, or the like.

In a preferred embodiment of the method of the invention, the Aβ40 inhibitor administered to the subject is comprised of at least one sulfonate group covalently attached to a carrier group, or a pharmaceutically acceptable salt thereof. Accordingly, an Aβ40 inhibitor can have the structure:

Q-[—SO$_3^-$X$^+$]$_n$ wherein Q is a carrier group; X$^+$ is a cationic group; and n is an integer. Suitable carrier groups and cationic groups are those described hereinbefore. The number of sulfonate groups ("n") is selected such that the biodistribution of the compound for an intended target site is not prevented while maintaining activity of the compound as discussed earlier. In one embodiment, n is an integer between 1 and 10. In another embodiment, n is an integer between 3 and 8. As described earlier, an Aβ40 inhibitor with multiple sulfonate groups can have the sulfonate groups spaced such that the compound interacts optimally with an HSPG binding site within the Aβ40 peptide.

In preferred embodiments, the carrier group for a sulfonate(s) is a lower aliphatic group (e.g., a lower alkyl, lower alkenyl or lower alkynyl), a heterocyclic group, and group derived from a disaccharide, a polymer or a peptide or peptide derivative. Furthermore, the carrier can be substituted, e.g., with one or more amino, nitro, halogeno, sulfhydryl or hydroxyl groups. In certain embodiments, the carrier for a sulfonate(s) is an aromatic group.

Examples of suitable sulfonated polymeric Aβ40 inhibitors include poly(2-acrylamido-2-methyl-1-propanesulfonic acid); poly(2-acrylamido-2-methyl-1-propanesulfonic acid-co-acrylonitrile); poly(2-acrylamido-2-methyl-1-propanesulfonic acid-co-styrene); poly(vinylsulfonic acid); poly(4-styrenesulfonic acid); a sulfonic acid derivative of poly(acrylic acid); a sulfonic acid derivative of poly(methyl acrylate); a sulfonic acid derivative of poly(methyl methacrylate); and pharmaceutically acceptable salts thereof.

A preferred sulfonated polymer is poly(vinylsulfonic acid) (PVS) or a pharmaceutically acceptable salt thereof, preferably the sodium salt thereof. In one embodiment, PVS having a molecular weight of about 800–1000 Daltons is used. PVS may be used as a mixture of isomers or as a single active isomer.

Preferred sulfonated saccharides include 5-deoxy-1,2-O-isopropylidene-α-D-xylofuranose-5-sulfonic acid (XXIII, shown as the sodium salt).

Preferred lower aliphatic sulfonated Aβ40 inhibitors for use in the invention include ethanesulfonic acid; 2-aminoethanesulfonic acid (taurine); cysteic acid (3-sulfoalanine or α-amino-β-sulfopropionic acid); 1-propanesulfonic acid; 1,2-ethanedisulfonic acid; 1,3-propanedisulfonic acid; 1,4-butanedisulfonic acid; 1,5-pentanedisulfonic acid; and 4-hydroxy-1-butanesulfonic acid (VIII, shown as the sodium salt); and pharmaceutically acceptable salts thereof. Other aliphatic sulfonated Aβ40 inhibitors contemplated for use in the invention include 1-butanesulfonic acid (XLVII, shown as the sodium salt), 2-propanesulfonic acid (XLIX, shown as the sodium salt), 3-pentanesulfonic acid (L, shown as the sodium salt), 4-heptanesulfonic acid (LII, shown as the sodium salt), 1-decanesulfonic acid (XLVIII, shown as the sodium salt); and pharmaceutically acceptable salts thereof. Sulfonated substituted aliphatic Aβ40 inhibitors contemplated for use in the invention include 3-amino-1-propanesulfonic acid (XXII, shown as the sodium salt), 3-hydroxy-1-propanesulfonic acid sulfate (XXXV, shown as the disodium salt), 1,7-dihydroxy-4-heptanesulfonic acid (LIII, shown as the sodium salt); and pharmaceutically acceptable salts thereof. Yet other sulfonated compounds contemplated for use in the invention include 2-[(4-pyridinyl)amido]ethanesulfonic acid (LIV, depicted as the sodium salt), and pharmaceutically acceptable salts thereof.

Preferred heterocyclic sulfonated Aβ40 inhibitors include 3-(N-morpholino)-1-propanesulfonic acid; and tetrahydrothiophene-1,1-dioxide-3,4-disulfonic acid; and pharmaceutically acceptable salts thereof.

Aromatic sulfonated Aβ40 inhibitors include 1,3-benzenedisulfonic acid (XXXVI, shown as the disodium salt), 2,5-dimethoxy-1,4-benzenedisulfonic acid (depicted as the disodium salt, XXXVII, or the dipotassium salt, XXXIX), 4-amino-3-hydroxy-1-naphthalenesulfonic acid (XLIII), 3,4-diamino-1-naphthalenesulfonic acid (XLIV); and pharmaceutically acceptable salts thereof.

In another embodiment of the method of the invention, the Aβ40 inhibitor administered to the subject is comprised of at least one sulfate group covalently attached to a carrier group, or a pharmaceutically acceptable salt thereof. Accordingly, the Aβ40 inhibitor can have the structure:

Q-[—OSO$_3^-$X$^+$]$_n$ wherein Q is a carrier group; X$^+$ is a cationic group; and n is an integer. Suitable carriers and cationic groups are those described hereinbefore. The number of sulfate groups ("n") is selected such that the biodistribution of the compound for an intended target site is not prevented while maintaining activity of the Aβ40 inhibitor as discussed earlier. In one embodiment, n is an integer between 1 and 10. In another embodiment, n is an integer between 3 and 8. As described earlier, an Aβ40 inhibitor with multiple sulfate groups can have the sulfate groups spaced such that the compound interacts optimally with a GAG binding site within an Aβ peptide.

In preferred embodiments, the carrier group for a sulfate (s) is a lower aliphatic group (e.g., a lower alkyl, lower alkenyl or lower alkynyl), an aromatic group, a group derived from a disaccharide, a polymer or a peptide or peptide derivative. Furthermore, the carrier can be substituted, e.g., with one or more amino, nitro, halogeno, sulfhydryl or hydroxyl groups.

Examples of suitable sulfated polymeric Aβ40 inhibitors include poly(2-acrylamido-2-methyl-1-propyl sulfuric acid); poly(2-acrylamido-2-methyl-1-propyl sulfuric acid-co-acrylonitrile); poly(2-acrylamido-2-methyl-propyl sulfuric acid-co-styrene); poly(vinylsulfuric acid); poly(sodium 4-styrenesulfate); a sulfate derivative of poly(acrylic acid); a sulfate derivative of poly(methyl acrylate); a sulfate derivative of poly(methyl methacrylate); and a sulfate derivative of poly(vinyl alcohol); and pharmaceutically acceptable salts thereof.

A preferred sulfated polymer is poly(vinylsulfuric acid) or pharmaceutically acceptable salt thereof.

A preferred sulfated disaccharide is sucrose octasulfate or pharmaceutically acceptable salt thereof. Other sulfated saccharides contemplated for use in the invention include the acid form of methyl α-D-glucopyranoside 2,3-disulfate (XVI), methyl 4,6-O-benzylidene-α-D-glucopyranoside 2,3-disulfate (XVII), 2,3,4,3',4'-sucrose pentasulfate (XXXIII), 1,3:4,6-di-O-benzylidene-D-mannitol 2,5-disulfate (XLI), D-mannitol 2,5-disulfate (XLII), 2,5-di-O- benzyl-D-mannitol tetrasulfate (XLV); and pharmaceutically acceptable salts thereof.

Preferred lower aliphatic sulfated Aβ40 inhibitors for use in the invention include ethyl sulfuric acid; 2-aminoethan-1-ol sulfuric acid; 1-propanol sulfuric acid; 1,2-ethanediol disulfuric acid; 1,3-propanediol disulfuric acid; 1,4-butanediol disulfuric acid; 1,5-pentanediol disulfuric acid; and 1,4-butanediol monosulfuric acid; and pharmaceutically acceptable salts thereof. Other sulfated aliphatic Aβ40 inhibitors contemplated for use in the invention include the acid form of 1,3-cyclohexanediol disulfate (XL), 1,3,5-heptanetriol trisulfate (XIX), 2-hydroxymethyl-1,3-propanediol trisulfate (XX), 2-hydroxymethyl-2-methyl-1,3-propanediol trisulfate (XXI), 1,3,5,7-heptanetetraol tetrasulfate (XLVI), 1,3,5,7,9-nonane pentasulfate (LI); and pharmaceutically acceptable salts thereof. Other sulfated Aβ40 inhibitors contemplated for use in the invention include the acid form of 2-amino-2-hydroxymethyl-1,3-propanediol trisulfate (XXIV), 2-benzyloxy-1,3-propanediol disulfate (XXIX), 3-hydroxypropylsulfamic acid sulfate (XXX), 2,2'-iminoethanol disulfate (XXXI), N,N-bis(2-hydroxyethyl)sulfamic acid disulfate (XXXII); and pharmaceutically acceptable salts thereof.

Preferred heterocyclic sulfated Aβ40 inhibitors include 3-(N-morpholino)-1-propyl sulfuric acid; and tetrahydrothiophene-3,4-diol-1,1-dioxide disulfuric acid; and pharmaceutically acceptable salts thereof.

The invention further contemplates the use of prodrugs which are converted in vivo to the Aβ40 inhibitors used in the methods of the invention (see, e.g., R. B. Silverman, 1992, "The Organic Chemistry of Drug Design and Drug Action", Academic Press, Chp. 8). Such prodrugs can be used to alter the biodistribution (e.g., to allow compounds which would not typically cross the blood-brain barrier to cross the blood-brain barrier) or the pharmacokinetics of the Aβ40 inhibitor. For example, an anionic group, e.g., a sulfate or sulfonate, can be esterified, e.g, with a methyl group or a phenyl group, to yield a sulfate or sulfonate ester. When the sulfate or sulfonate ester is administered to a subject, the ester is cleaved, enzymatically or non-enzymatically, reductively or hydrolytically, to reveal the anionic group. Such an ester can be cyclic, e.g., a cyclic sulfate or sultone, or two or more anionic moieties may be esterified through a linking group. Exemplary cyclic Aβ40 inhibitors include, for example, 2-sulfobenzoic acid cyclic anhydride (LV), 1,3-propane sultone (LVI), 1,4-butane sultone (LVII), 1,3-butanediol cyclic sulfate (LVIII), α-chloro-α-hydroxy-o-toluenesulfonic acid γ-sultone (LIX), and 6-nitronaphth-[1,8-cd]-1,2,-oxathiole 2,2-dioxide (LX). In a preferred embodiment, the prodrug is a cyclic sulfate or sultone. An anionic group can be esterified with moieties (e.g., acyloxymethyl esters) which are cleaved to reveal an intermediate Aβ40 inhibitor which subsequently decomposes to yield the active Aβ40 inhibitor. In another embodiment, the prodrug is a reduced form of a sulfate or sulfonate, e.g., a thiol, which is oxidized in vivo to the Aβ40 inhibitor. Furthermore, an anionic moiety can be esterified to a group which is actively transported in vivo, or which is selectively taken up by target organs. The ester can be selected to allow specific targeting of the Aβ40 inhibitors to particular organs, as described below for carrier moieties.

Carrier groups useful in the Aβ40 inhibitors include groups previously described, e.g., aliphatic groups, alicyclic groups, heterocyclic groups, aromatic groups, groups derived from carbohydrates, polymers, peptides, peptide derivatives, or combinations thereof. Suitable polymers include substituted and unsubstituted vinyl, acryl, styrene and carbohydrate-derived polymers and copolymers and salts thereof. Preferred carrier groups include a lower alkyl group, a heterocyclic group, a group derived from a disaccharide, a polymer, a peptide, or peptide derivative.

Carrier groups useful in the present invention may also include moieties which allow the Aβ40 inhibitor to be selectively delivered to a target organ or organs. For example, for a desirable delivery of an Aβ40 inhibitor to the brain, the carrier group may include a moiety capable of targeting the Aβ40 inhibitor to the brain, by either active or passive transport (a "targeting moiety"). Illustratively, the carrier group may include a redox moiety, as described in, for example, U.S. Pat. Nos. 4,540,564 and 5,389,623, both to Bodor. These patents disclose drugs linked to dihydropyridine moieties which can enter the brain, where they are oxidized to a charged pyridinium species which is trapped in the brain. Thus, drug accumulates in the brain. Exemplary pyridine/dihydropyridine compounds of the invention include sodium 2-(nicotinylamido)-ethanesulfonate (LXII), and 1-(3-sulfopropyl)-pyridinium betaine (LXIII). Other carrier moieties include groups, such as those derived from amino acids or thyroxine, which can be passively or actively transported in vivo. An illustrative compound is phenylalanyltaurine (LXIX), in which a taurine molecule is conjugated to a phenylalanine (a large neutral amino acid). Such a carrier moiety can be metabolically removed in vivo, or can remain intact as part of an active Aβ40 inhibitor. Structural mimics of amino acids (and other actively transported moieties) are also useful in the invention (e.g., 1-(aminomethyl)-1-(sulfomethyl)-cyclohexane (LXX)). Other exemplary amino acid mimetics include p-(sulfomethyl)phenylalanine (LXXII), p-(1,3-disulfoprop-2-yl)phenylalanine (LXXIII), and O-(1,3-disulfoprop-2-yl) tyrosine (LXXIV). Exemplary thyroxine mimetics include compounds LXXV, LXVI, and LXXVII. Many targeting moieties are known, and include, for example, asialoglycoproteins (see, e.g., Wu, U.S. Pat. No. 5,166,320) and other ligands which are transported into cells via receptor-mediated endocytosis (see below for further examples of targeting moieties which may be covalently or non-covalently bound to a carrier molecule). Furthermore, the Aβ40 inhibitors of the invention may bind to amyloidogenic proteins, e.g., Aβ40, in the circulation and thus be transported to the site of action.

The targeting and prodrug strategies described above can be combined to produce an Aβ40 inhibitor that can be transported as a prodrug to a desired site of action and then unmasked to reveal an active Aβ40 inhibitor. For example, the dihydropyridine strategy of Bodor (see supra) can be combined with a cyclic prodrug, as for example in the compound 2-(1-methyl-1,4-dihydronicotinoyl) amidomethyl-propanesultone (LXXI).

In one embodiment, the Aβ40 inhibitor in the pharmaceutical compositions is a sulfonated polymer, for example poly(2-acrylamido-2-methyl-1-propanesulfonic acid); poly (2-acrylamido-2-methyl-1-propanesulfonic acid-co-acrylonitrile); poly(2-acrylamido-2-methyl-1-propanesulfonic acid-co-styrene); poly(vinylsulfonic acid); poly(4-styrenesulfonic acid); a sulfonate derivative of poly (acrylic acid); a sulfonate derivative of poly(methyl acrylate); a sulfonate derivative of poly(methyl methacrylate); and a sulfonate derivative of poly(vinyl alcohol); and pharmaceutically acceptable salts thereof.

In another embodiment, the Aβ40 inhibitor in the pharmaceutical compositions is a sulfated polymer, for example poly(2-acrylamido-2-methyl-1-propyl sulfuric acid); poly (2-acrylamido-2-methyl-1-propyl sulfuric acid-coacrylonitrile); poly(2-acrylamido-2-methyl-1-propyl sulfuric acid-co-styrene); poly(vinyl sulfuric acid); poly(4-styrenesulfate); a sulfate derivative of poly(acrylic acid); a sulfate derivative of poly(methyl acrylate); a sulfate derivative of poly(methyl methacrylate); and pharmaceutically acceptable salts thereof.

The Aβ40 inhibitor can also have the structure:

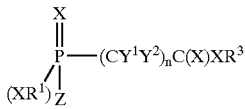

wherein Z is $XR^2$ or $R^4$, $R^1$ and $R^2$ are each independently hydrogen, a substituted or unsubstituted aliphatic group (preferably a branched or straight-chain aliphatic moiety having from 1 to 24 carbon atoms in the chain; or an unsubstituted or substituted cyclic aliphatic moiety having from 4 to 7 carbon atoms in the aliphatic ring; preferred aliphatic and cyclic aliphatic groups are alkyl groups, more preferably lower alkyl), an aryl group, a heterocyclic group, or a salt-forming cation; $R^3$ is hydrogen, lower alkyl, aryl, or a salt-forming cation; X is, independently for each occurrence, O or S; $R^4$ is hydrogen, lower alkyl, aryl or amino; $Y^1$ and $Y^2$ are each independently hydrogen, halogen (e.g., F, Cl, Br, or I), lower alkyl, amino (including alkylamino, dialkylamino, arylamino, diarylamino, and alkylarylamino), hydroxy, alkoxy, or aryloxy; and n is an integer from 0 to 12 (more preferably 0 to 6, more preferably 0 or 1). These compounds are described in U.S. Pat. No. 5,869,469, the contents of which is incorporated herein by reference.

Preferred Aβ40 inhibitors for use in the invention include compounds in which both $R^1$ and $R^2$ are pharmaceutically acceptable salt-forming cations. It will be appreciated that the stoichiometry of an anionic compound to a salt-forming counterion (if any) will vary depending on the charge of the anionic portion of the compound (if any) and the charge of the counterion. In a particularly preferred embodiment, $R^1$, $R^2$ and $R^3$ are each independently a sodium, potassium or calcium cation. In certain embodiments in which at least one of $R^1$ and $R^2$ is an aliphatic group, the aliphatic group has between 1 and 10 carbons atoms in the straight or branched chain, and is more preferably a lower alkyl group. In other embodiments in which at least one of $R^1$ and $R^2$ is an aliphatic group, the aliphatic group has between 10 and 24 carbons atoms in the straight or branched chain. In certain preferred embodiments, n is 0 or 1; more preferably, n is 0. In certain preferred embodiments of the therapeutic compounds, $Y^1$ and $Y^2$ are each hydrogen.

In certain preferred embodiments, the Aβ40 inhibitor of the invention can have the structure:

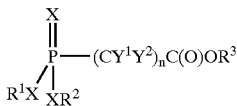

in which $R^1$, $R^2$, $R^3$, $Y^1$, $Y^2$, X and n are as defined above. In more preferred embodiments, the Aβ40 inhibitor of the invention can have the structure:

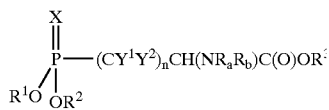

wherein $R^1$, $R^2$, $R^3$, $Y^1$, $Y^2$, and X are as defined above, $R_a$ and $R_b$ are each independently hydrogen, alkyl, aryl, or heterocyclyl, or $R_a$ and $R_b$, taken together with the nitrogen atom to which they are attached, form a cyclic moiety having from 3 to 8 atoms in the ring, and n is an integer from 0 to 6. In certain preferred embodiments, $R_a$ and $R_b$ are each hydrogen. In certain preferred embodiments, a compound of the invention comprises an α-amino acid (or α-amino acid ester), more preferably a L-α-amino acid or ester.

The Z, $R^1$, $R^2$, $R^3$, $Y^1$, $Y^2$ and X groups are each independently selected such that the biodistribution of the Aβ40 inhibitor for an intended target site is not prevented while maintaining activity of the Aβ40 inhibitor. For example, the number of anionic groups (and the overall charge on the therapeutic compound) should not be so great as to prevent traversal of an anatomical barrier, such as a cell membrane, or entry across a physiological barrier, such as the blood-brain barrier, in situations where such properties are desired. For example, it has been reported that esters of phosphonoformate have biodistribution properties different from, and in some cases superior to, the biodistribution properties of phosphonoformate (see, e.g., U.S. Pat. Nos. 4,386,081 and 4,591,583 to Helgstrand et al., and U.S. Pat. Nos. 5,194,654 and 5,463,092 to Hostetler et al.). Thus, in certain embodiments, at least one of $R^1$ and $R^2$ is an aliphatic group (more preferably an alkyl group), in which the aliphatic group has between 10 and 24 carbons atoms in the straight or branched chain. The number, length, and degree of branching of the aliphatic chains can be selected to provide a desired characteristic, e.g., lipophilicity. In other embodiments, at least one of $R^1$ and $R^2$ is an aliphatic group (more preferably an alkyl group), in which the aliphatic group has between 1 and 10 carbons atoms in the straight or branched chain. Again, the number, length, and degree of branching of the aliphatic chains can be selected to provide a desired characteristic, e.g., lipophilicity or ease of ester cleavage by enzymes. In certain embodiments, a preferred aliphatic group is an ethyl group.

In another embodiment, the Aβ40 inhibitor of the invention can have the structure:

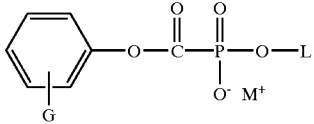

wherein G represents hydrogen or one or more substituents on the aryl ring (e.g., alkyl, aryl, halogen, amino, and the like) and L is a substituted alkyl group (in certain embodiments, preferably a lower alkyl), more preferably a hydroxy-substituted alkyl or an alkyl substituted with a nucleoside base, and $M^+$ is a counter ion. In certain embodiments, G is hydrogen or an electron-donating group. In embodiments in which G is an electron-withdrawing group, G is preferably an electron withdrawing group at the meta position. The term "electron-withdrawing group" is known in the art, and, as used herein, refers to a group which has a greater electron-withdrawing than hydrogen. A variety of electron-withdrawing groups are known, and include halogens (e.g., fluoro, chloro, bromo, and iodo groups), nitro, cyano, and the like. Similarly, the term "electron-donating group", as used herein, refers to a group which is less electron-withdrawing than hydrogen. In embodiments in which G is an electron donating group, G can be in the ortho, meta or para position. In certain embodiments, $M^+$ is a cationic species selected from, e.g., $H^+$ and pharmaceutically acceptable organic or inorganic ions, including, without limitation, $Na^+$, $K^+$, $NH_4^+$, $Ca^{+2}$, $RNH_3^+$, $RR'NH_2^+$. In one preferred embodiment, M+ is an anilinium ion.

In certain preferred embodiments, L may be one of the following moieties:

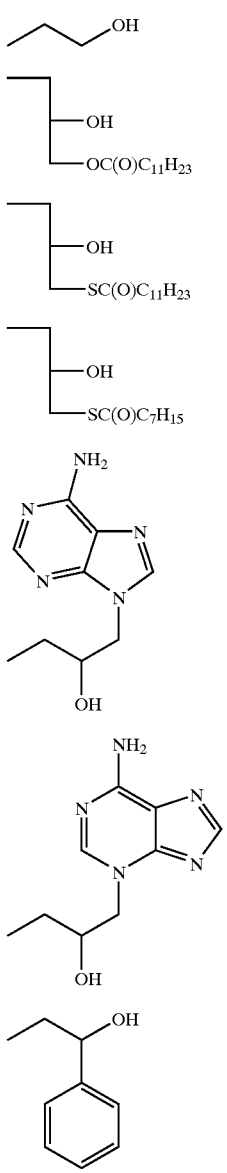

IVa

IVb

IVc

IVd

IVe

IVf

IVg

Table 1 lists data pertinent to the characterization of these compounds using art-recognized techniques. The compounds IVa–IVg in Table 1 correspond to the following structure, wherein L is a group selected from the above-listed (Groups IVa–IVg) having the same number.

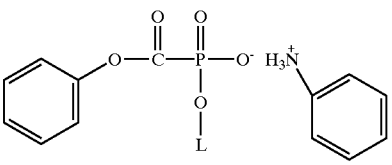

TABLE 1

| COMPOUND | $^{31}P$ NMR | $^{13}C$ NMR | FAB-MS(−) |
|---|---|---|---|
| IVa | −6.33 (DMSO-$d_6$) | 60.97 $CH_2OH$(d,J=6 Hz) 66.76 CHOH(d,J=7.8 Hz) 121.65, 121.78, 121.99, 125.71, 129.48, 129.57, 126.43 Aromatic CH 134.38 Aniline C-N 150.39 Phenyl C-O (d,J=7 Hz) 171.57 P-C=O(d,J=234 Hz) | 245.2 |
| IVb | −6.41 (DMSO-$d_6$) | 13.94 $CH_3$ 22.11, 24.40, 28.56, 28.72, 28.99, 29.00, 31.30, 33.43, -$(CH_2)_{10}$- 65.03 $CH_2$-OC(O) 66.60 $CH_2$-OP(d,J'25.6 Hz) 67.71 $CH_2$-OH(d,J=6 Hz) 121.73, 121.10, 125.64, 126.57, 129.40, 129.95, Aromatic CH 134.04 Aniline C-N 150.31 Phenyl C-O 171.44 P-C=O(d,J=6.7 Hz) 172.83 O-C=O | 456 |
| IVc | −6.46 (DMSO-$d_6$) | 13.94 $CH_3$ 22.11, 25.10, 28.68, 28.72, 28.85, 29.00, 30.76, 31.31, 32.10, -$(CH_2)_{10}$- 43.36 $CH_2$-S 68.43 $CH_2$-OH 68.43 CH-OH(d,J=6.3 Hz) 68.76 P-O-$CH_2$- 9d,J=5.8 Hz) 121.75, 122.03, 125.62, 126.37, 129.30, 129.53, Aromatic CH 134.23 Aniline C-N 150.37 Phenyl C-O (d,J=6.7 Hz) 171.47 P-C=O (d,J=234.0 Hz) 198.47 S-C=O | 471 |
| IVd | −6.61 (DMSO-$d_6$) | 13.94 $CH_3$ 22.06, 25.14, 28.24, 28.35, 31.09, 32.14 -$(CH_2)_6$- 43.40 $CH_2$-S 68.50 P-O-$CH_2$- (d,J=5.8 Hz) 68.77 CH-OH(d, 6.4 Hz) 121.78, 122.59, 125.69, 127.06, 129.43, 129.59 Aromatic CH 133.39 Aniline C-N 150.38 Phenyl C-O (d,J=6.7 Hz) 171.47 P-C=O (d,J=234.4 Hz) 198.54 S-C=O | 416 |
| IVe | −5.76 ($D_2O$) | N/A | N/A |
| IVf | −7.00 (DMSO-$d_6$) | N/A | N/A |
| IVg | −6.60 (DMSO-$d_6$) | 70.84 CH2-OH 72.17 CH-OH 121.68, 121.79, 121.85, 125.71 127.10, 127.92, | 321 |

TABLE 1-continued

| COMPOUND | $^{31}$P NMR | $^{13}$C NMR | FAB-MS(−) |
|---|---|---|---|
| | | 129.36, 129.50, 129.59 Aromatic CH | |
| | | 134.51 Aniline C-N | |
| | | 142.34 Aromatic C-CH | |
| | | 150.37 Phenyl C-O (d,J=6.2 Hz) | |
| | | 171.59 P-C=O (d,J=232.6 Hz) | |

Note that the structure of some of the Aβ40 inhibitors of this invention includes asymmetric carbon atoms. It is to be understood accordingly that the isomers (e.g., enantiomers and diastereomers) arising from such asymmetry are included within the scope of this invention. Such isomers can be obtained in substantially pure form by classical separation techniques and by sterically controlled synthesis. For the purposes of this application, unless expressly noted to the contrary, an Aβ40 inhibitor shall be construed to include both the R or S stereoisomers at each chiral center.

In certain embodiments, an Aβ40 inhibitor of the invention comprises a cation (i.e., in certain embodiments, at least one of $R^1$, $R^2$ or $R^3$ is a cation). If the cationic group is hydrogen, $H^+$, then the Aβ40 inhibitor is considered an acid, e.g., phosphonoformic acid. If hydrogen is replaced by a metal ion or its equivalent, the Aβ40 inhibitor is a salt of the acid. Pharmaceutically acceptable salts of the Aβ40 inhibitor are within the scope of the invention. For example, at least one of $R^1$, $R^2$ or $R^3$ can be a pharmaceutically acceptable alkali metal (e.g., Li, Na, or K), ammonium cation, alkaline earth cation (e.g., $Ca^{2+}$, $Ba^{2+}$, $Mg^{2+}$), higher valency cation, or polycationic counter ion (e.g., a polyammonium cation). (See, e.g., Berge et al. (1977) "Pharmaceutical Salts", *J. Pharm. Sci.* 66: 1–19). It will be appreciated that the stoichiometry of an anionic compound to a salt-forming counterion (if any) will vary depending on the charge of the anionic portion of the compound (if any) and the charge of the counterion. Preferred pharmaceutically acceptable salts include a sodium, potassium or calcium salt, but other salts are also contemplated within their pharmaceutically acceptable range.

The term "pharmaceutically acceptable esters" refers to the relatively non-toxic, esterified products of the Aβ40 inhibitors of the present invention. These esters can be prepared in situ during the final isolation and purification of the Aβ40 inhibitors or by separately reacting the purified Aβ40 inhibitor in its free acid form or hydroxyl with a suitable esterifying agent; either of which are methods known to those skilled in the art. Carboxylic acids and phosphonic acids can be converted into esters according to methods well known to one of ordinary skill in the art, e.g., via treatment with an alcohol in the presence of a catalyst. A preferred ester group (e.g., when $R^3$ is lower alkyl) is an ethyl ester group.

The term "alkyl" refers to the saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 4–7 carbon atoms in the ring structure. The term "lower alkyl" refers to alkyl groups having from 1 to 6 carbons in the chain, and to cycloalkyls having from 3 to 6 carbons in the ring structure.

Moreover, the term "alkyl" (including "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (benzyl)).

The term "alkoxy", as used herein, refers to a moiety having the structure —O-alkyl, in which the alkyl moiety is described above.

The term "aryl" as used herein includes 5- and 6-membered single-ring aromatic groups that may include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. The aromatic ring can be substituted at one or more ring positions with such substituents, e.g., as described above for alkyl groups. Preferred aryl groups include unsubstituted and substituted phenyl groups.

The term "aryloxy", as used herein, refers to a group having the structure —O-aryl, in which the aryl moiety is as defined above.

The term "amino," as used herein, refers to an unsubstituted or substituted moiety of the formula —$NR_aR_b$, wherein $R_a$ and $R_b$ are each independently hydrogen, alkyl, aryl, or heterocyclyl, or $R_a$ and $R_b$, taken together with the nitrogen atom to which they are attached, form a cyclic moiety having from 3 to 8 atoms in the ring. Thus, the term "amino" is intended to include cyclic amino moieties such as piperidinyl or pyrrolidinyl groups, unless otherwise stated. An "amino-substituted amino group" refers to an amino group in which at least one of $R_a$ and $R_b$, is further substituted with an amino group.

In a preferred embodiment, $R^1$ or $R^2$ can be (for at least one occurrence) a long-chain aliphatic moiety. The term "long-chain aliphatic moiety" as used herein, refers to a moiety having a straight or branched chain aliphatic moiety (e.g., an alkyl or alkenyl moiety) having from 10 to 24 carbons in the aliphatic chain, e.g., the long-chain aliphatic moiety is an aliphatic chain of a fatty acid (preferably a naturally-occurring fatty acid). Representative long-chain aliphatic moieties include the aliphatic chains of stearic acid, oleic acid, linolenic acid, and the like.

In certain embodiments, the Aβ40 inhibitor of the invention can have the structure:

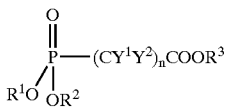

wherein $R^1$ and $R^2$ are each independently hydrogen, an aliphatic group (preferably a branched or straight-chain aliphatic moiety having from 1 to 24 carbon atoms, more preferably 10–24 carbon atoms, in the chain; or an unsubstituted or substituted cyclic aliphatic moiety having from 4 to 7 carbon atoms in the aliphatic ring), an aryl group, a heterocyclic group, or a salt-forming cation; $R^3$ is hydrogen, lower alkyl, aryl, or a salt-forming cation; $Y^1$ and $Y^2$ are each independently hydrogen, halogen (e.g., F, Cl, Br, or I), lower alkyl, hydroxy, alkoxy, or aryloxy; and n is an integer from 0 to 12. Preferred Aβ40 inhibitors for use in the invention include compounds wherein both $R^1$ and $R^2$ are pharmaceutically acceptable salt-forming cations. In a particularly preferred embodiment, $R^1$, $R^2$ and $R^3$ are each independently a sodium, potassium or calcium cation, and n is 0. In certain preferred embodiments of the therapeutic compounds, $Y^1$ and $Y^2$ are each hydrogen. Particularly preferred Aβ40 inhibitors are salts of phosphonoformate. Trisodium phosphonoformate (foscarnet sodium or Foscavir®) is commercially available (e.g., from Astra), and its clinical pharmacology has been investigated (see, e.g., "Physician's Desk Reference", 51st Ed., pp. 541–545 (1997)).

In another embodiment, the Aβ40 inhibitor used in the invention can be an aminophosphonate, a bisphosphonate, a phosphonocarboxylate derivative, a phosphonate derivative, or a phosphono carbohydrate. For example, the Aβ40 inhibitor can be one of the compounds described in Tables III and IV.

The present invention also pertains to a method of diagnosing cerebral amyloid angiopathy in a subject, the method comprising administering an imageable Aβ40 inhibitor to said subject in such a manner that the imageable Aβ40 inhibitor is allowed to contact cerebral blood vessels which are likely areas for cerebral amyloid angiopathy, and imaging said areas to determine the presence or absence of the imageable Aβ40 inhibitor in the areas such that diagnosis can be made.

Pharmaceutically Acceptable Formulations

In the methods of the invention, the Aβ40 inhibitor can be administered in a pharmaceutically acceptable formulation. The present invention pertains to any pharmaceutically acceptable formulations, such as synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes.

In one embodiment, the pharmaceutically acceptable formulations comprise a polymeric matrix.

The terms "polymer" or "polymeric" are art-recognized and include a structural framework comprised of repeating monomer units which is capable of delivering an Aβ40 inhibitor, such that treatment of a targeted condition occurs. The terms also include co-polymers and homopolymers e.g., synthetic or naturally occurring. Linear polymers, branched polymers, and cross-linked polymers are also meant to be included.

For example, polymeric materials suitable for forming the pharmaceutically acceptable formulation employed in the present invention, include naturally derived polymers such as albumin, alginate, cellulose derivatives, collagen, fibrin, gelatin, and polysaccharides, as well as synthetic polymers such as polyesters (PLA, PLGA), polyethylene glycol, poloxomers, polyanhydrides, and pluronics. These polymers are biocompatible and biodegradable without producing any toxic byproducts of degradation, and they possess the ability to modify the manner and duration of Aβ40 inhibitor release by manipulating the polymer's kinetic characteristics. As used herein, the term "biodegradable" means that the polymer will degrade over time by the action of enzymes, by hydrolytic action and/or by other similar mechanisms in the body of the subject. As used herein, the term "biocompatible" means that the polymer is compatible with a living tissue or a living organism by not being toxic or injurious and by not causing an immunological rejection.

Polymers can be prepared using methods known in the art (Sandler, S. R.; Karo, W. *Polymer Syntheses*; Harcourt Brace: Boston, 1994; Shalaby, W.; Ikada, Y.; Langer, R.; Williams, J. *Polymers of Biological and Biomedical Significance* (*ACS Symposium Series* 540; American Chemical Society: Washington, DC, 1994). Polymers can be designed to be flexible; the distance between the bioactive side-chains and the length of a linker between the polymer backbone and the group can be controlled. Other suitable polymers and methods for their preparation are described in U.S. Pat. Nos. 5,455,044 and 5,576,018.

The polymeric formulations are preferably formed by dispersion of the Aβ40 inhibitor within liquefied polymer, as described in U.S. Pat. No. 4,883,666, the teachings of which are incorporated herein by reference, or by such methods as bulk polymerization, interfacial polymerization, solution polymerization and ring polymerization as described in Odian G., *Principles Of Polymerization And Ring Opening Polymerization*, 2nd ed., John Wiley & Sons, New York, 1981. The properties and characteristics of the formulations are controlled by varying such parameters as the reaction temperature, concentrations of polymer and Aβ40 inhibitor, types of solvent used, and reaction times.

In addition to the Aβ40 inhibitor and the pharmaceutically acceptable polymer, the pharmaceutically acceptable formulation used in the method of the invention can comprise additional pharmaceutically acceptable carriers and/or excipients. As used herein, "pharmaceutically acceptable carrier" includes any and all solvents, dispersion media, coatings, antibacterial and antifungal agents, isotonic and absorption delaying agents, and the like that are physiologically compatible. For example, the carrier can be suitable for injection into the cerebrospinal fluid. Excipients include pharmaceutically acceptable stabilizers and disintegrants.

The Aβ40 inhibitor can be encapsulated in one or more pharmaceutically acceptable polymers, to form a microcapsule, microsphere, or microparticle, terms used herein interchangeably. Microcapsules, microspheres, and microparticles are conventionally free-flowing powders consisting of spherical particles of 2 mm or less in diameter, usually 500 μm or less in diameter. Particles less than 1 μm are conventionally referred to as nanocapsules, nanoparticles or nanospheres. For the most part, the difference between a microcapsule and a nanocapsule, a microsphere and a nanosphere, or microparticle and nanoparticle is size; generally there is little, if any, difference between the internal structure of the two. In one aspect of the present invention, the mean average diameter is less than about 45 μm, preferably less than 20 μm, and more preferably between about 0.1 and 10 μm.

In another embodiment, the pharmaceutically acceptable formulations comprise lipid-based formulations. Any of the known lipid-based drug delivery systems can be used in the practice of the invention. For instance, multivesicular liposomes (MVL), multilamellar liposomes (also known as multilamellar vesicles or "MLV"), unilamellar liposomes, including small unilamellar liposomes (also known as unilamellar vesicles or "SUV") and large unilamellar liposomes (also known as large unilamellar vesicles or "LUV"), can all be used so long as a sustained release rate of the encapsulated Aβ40 inhibitor can be established. In one embodiment, the lipid-based formulation can be a multivesicular liposome system. Methods of making controlled release multivesicular liposome drug delivery systems is described in PCT Application Nos. US96/11642, US94/12957 and US94/04490.

The composition of the synthetic membrane vesicle is usually a combination of phospholipids, usually in combination with steroids, especially cholesterol. Other phospholipids or other lipids may also be used.

Examples of lipids useful in synthetic membrane vesicle production include phosphatidylglycerols, phosphatidylcholines, phosphatidylserines, phosphatidylethanolamines, sphingolipids, cerebrosides, and gangliosides. Preferably phospholipids including egg phosphatidylcholine, dipalmitoylphosphatidylcholine, distearoylphosphatidylcholine, dioleoylphosphatidylcholine, dipalmitoylphosphatidylglycerol, and dioleoylphosphatidylglycerol are used.

In preparing lipid-based vesicles containing an Aβ40 inhibitor, such variables as the efficiency of Aβ40 inhibitor encapsulation, lability of the Aβ40 inhibitor, homogeneity and size of the resulting population of vesicles, Aβ40 inhibitor-to-lipid ratio, permeability, instability of the preparation, and pharmaceutical acceptability of the formulation should be considered (see Szoka, et al., *Annual Reviews of Biophysics and Bioengineering*, 9: 467, 1980; Deamer, et al., in *Liposomes*, Marcel Dekker, New York, 1983, 27; and Hope, et al., *Chem. Phys. Lipids*, 40: 89, 1986, the contents of which are incorporated herein by reference).

Administration of the Pharmaceutically Acceptable Formulation

The Aβ40 inhibitor may be administered to a subject, e.g., parenterally, e.g., intravenously, intradermally, subcutaneously, orally (e.g., via inhalation), transdermally (topically), transmucosally, or rectally. In one embodiment, the Aβ40 inhibitor is administered by introduction into the central nervous system of the subject, e.g., into the cerebrospinal fluid of the subject. In certain aspects of the invention, the Aβ40 inhibitor is introduced intrathecally, e.g., into a cerebral ventricle, the lumbar area, or the cisterna magna.

The pharmaceutically acceptable formulations can easily be suspended in aqueous vehicles and introduced through conventional hypodermic needles or using infusion pumps. Prior to introduction, the formulations can be sterilized with, preferably, gamma radiation or electron beam sterilization.

In another embodiment of the invention, the Aβ40 inhibitor formulation is administered into a subject intrathecally. As used herein, the term "intrathecal administration" is intended to include delivering an Aβ40 inhibitor formulation directly into the cerebrospinal fluid of a subject, by techniques including lateral cerebroventricular injection through a burrhole or cisternal or lumbar puncture or the like (described in Lazorthes et al. *Advances in Drug Delivery Systems and Applications in Neurosurgery*, 143–192 and Omaya et al., *Cancer Drug Delivery*, 1: 169–179, the contents of which are incorporated herein by reference). The term "lumbar region" is intended to include the area between the third and fourth lumbar (lower back) vertebrae. The term "cisterna magna" is intended to include the area where the skull ends and the spinal cord begins at the back of the head. The term "cerebral ventricle" is intended to include the cavities in the brain that are continuous with the central canal of the spinal cord. Administration of an Aβ40 inhibitor to any of the above mentioned sites can be achieved by direct injection of the Aβ40 inhibitor formulation or by the use of infusion pumps. For injection, the Aβ40 inhibitor formulation of the invention can be formulated in liquid solutions, preferably in physiologically compatible buffers such as Hank's solution or Ringer's solution. In addition, the Aβ40 inhibitor formulation may be formulated in solid form and re-dissolved or suspended immediately prior to use. Lyophilized forms are also included. The injection can be, for example, in the form of a bolus injection or continuous infusion (e.g., using infusion pumps) of the formulation.

Duration and Levels of Administration

In another embodiment of the method of the invention, the pharmaceutically acceptable formulation provides sustained delivery, e.g., "slow release" of the Aβ40 inhibitor to a subject for at least one, two, three, or four weeks after the pharmaceutically acceptable formulation is administered to the subject.

As used herein, the term "sustained delivery" is intended to include continual delivery of an Aβ40 inhibitor in vivo over a period of time following administration, preferably at least several days, a week or several weeks. Sustained delivery of the Aβ40 inhibitor can be demonstrated by, for example, the continued therapeutic effect of the Aβ40 inhibitor over time (e.g., sustained delivery of the Aβ40 inhibitor can be demonstrated by continued inhibition of cerebral amyloid angiopathy over time). Alternatively, sustained delivery of the Aβ40 inhibitor may be demonstrated by detecting the presence of the Aβ40 inhibitor in vivo over time.

In one embodiment, the pharmaceutically acceptable formulation provides sustained delivery of the Aβ40 inhibitor to a subject for less than 30 days after the Aβ40 inhibitor is administered to the subject. For example, the pharmaceutically acceptable formulation, e.g., "slow release" formulation, can provide sustained delivery of the Aβ40 inhibitor to a subject for one, two, three or four weeks after the Aβ40 inhibitor is administered to the subject. Alternatively, the pharmaceutically acceptable formulation may provide sustained delivery of the Aβ40 inhibitor to a subject for more than 30 days after the Aβ40 inhibitor is administered to the subject.

The pharmaceutical formulation, used in the method of the invention, contains a therapeutically effective amount of the Aβ40 inhibitor. A "therapeutically effective amount" refers to an amount effective, at dosages and for periods of time necessary, to achieve the desired result. A therapeutically effective amount of the Aβ40 inhibitor may vary according to factors such as the disease state, age, and weight of the subject, and the ability of the Aβ40 inhibitor (alone or in combination with one or more other agents) to elicit a desired response in the subject. Dosage regimens may be adjusted to provide the optimum therapeutic response. A therapeutically effective amount is also one in which any toxic or detrimental effects of the Aβ40 inhibitor are outweighed by the therapeutically beneficial effects. A non-limiting range for a therapeutically effective concentration of an Aβ40 inhibitor is 100 µM to 1 mM. It is to be further understood that for any particular subject, specific dosage regimens should be adjusted over time according to the individual need and the professional judgment of the person administering or supervising the administration of the Aβ40 inhibitor and that dosage ranges set forth herein are exemplary only and are not intended to limit the scope or practice of the claimed invention.

In Vitro Treatment of Blood Vessel Wall Cells

Blood vessel wall cells, or isolated blood vessel wall cells, can further be contacted with a therapeutically effective amount of a Aβ40 inhibitor, in vitro. Accordingly, such cells can be isolated from a subject and grown in vitro, using techniques well known in the art. Briefly, a smooth muscle cell culture can be obtained by allowing smooth muscle cells to migrate out of fragments of tissue adhering to a suitable substrate such as a culture dish, or by disaggregating the tissue, e.g., mechanically or enzymatically, to produce a suspension of cells. For example, the enzymes trypsin, collagenase, elastase, hyaluronidase, DNAse, pronase, dispase, or various combinations thereof can be used. Trypsin and pronase give the most complete disaggregation but may damage the cells. Collagenase and dispase give a less complete disaggregation but are less harmful. Methods for isolating tissue such as neuronal tissue, and the disaggregation of tissue to obtain cells such as neuronal cells are described in Freshney R. I., *Culture of Animal Cells, A Manual of Basic Technique, Third Edition*, 1994, the contents of which are incorporated herein by reference.

Such cells can be subsequently contacted with an Aβ40 inhibitor at levels and for a duration of time as described above. Once inhibition of cerebral amyloid angiopathy has been achieved, these neuronal cells can be re-administered to the subject, e.g., by implantation.

States Characterized by CAA

The present invention further pertains to a method of treating a disease state characterized by cerebral amyloid angiopathy in a subject. As used herein, the term "state" is art recognized and includes a disorder, disease or condition characterized by cerebral amyloid angiopathy. Examples of such disorders include Alzheimer's Disease, HCHWA-D, and hemorrhagic stroke.

The invention is further illustrated by the following examples, which should not be construed as further limiting. The contents of all references, patents and published patent applications cited throughout this application are hereby incorporated by reference.

EXAMPLE 1

A compound of the invention is administered in a therapeutic amount to a subject having a clinical diagnosis of 'probable CAA', defined for present purposes as: multiple hemorrhages confined to the lobar brain regions diagnosed by CT or MRI scan and no other cause of hemorrhage. The ability of the compound of the invention to prevent recurrence of CAA-related hemorrhages is determined by clinical exams (new neurologic symptoms or death with acute hemorrhage confirmed by CT scan or autopsy) or by gradient-echo MRI scans which mark the progression of CAA by the appearance of new hemorrhages. The ability of the compound to inhibit the progression of CAA can also be assessed through cognitive decline (MMSE) or functional decline (NIHSS, FIM). The APOE-2 and APOE-4 are associated with increasing risk and earlier age of first hemorrhage, but are neither specific nor sensitive for CAA.

EXAMPLE 2

The ability of compounds of the invention to inhibit CAA was measured in the following example. Nine week old hAPP transgenic mice were treated for a period of 8 weeks with two different concentrations of a compound of the present invention, 3-amino-1-propanesulfonic acid, sodium salt, 100 and 30 mg/kg. Mice were administered the compound for 8 weeks, after which they were sacrificed and their brains were perfused and processed for histological staining with Thioflavin S. This method may also be used as a screening method for determining activity of a candidate compound for inhibiting CAA.

The extent of CAA in brain sections obtained from these animals was qualitatively determined following staining. The extent of CAA, if any, was graded as follows:

+ Slight deposition

++ Moderate deposition

+++ Severe deposition

The results shown in Table II, below, indicate that the test compound was effective in 1) reducing the numnber of mice showing CAA, and 2) showing an effect on the severity of the deposition seen in the brain vasculature of these animals.

TABLE II

| Treatment | # animals in study | # of animals with CAA | CAA animals/ total animals | CAA Severity | | |
|---|---|---|---|---|---|---|
| | | | | + | ++ | +++ |
| Vehicle | 16 | 15 | 15/16 | 5/15 | 9/15 | 1/15 |
| 30 mg/kg | 11 | 10 | 10/11 | 6/10 | 4/10 | — |
| 100 mg · kg | 15 | 10 | 10/15 | 9/10 | — | 1/10 |

TABLE III

Phosphonoacetic acid

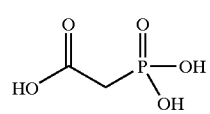

Phosphonoformic acid, trisodium salt hexahydrate

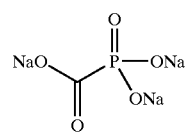

TABLE III-continued

| | |
|---|---|
| Diethylphosphonoacetic acid | 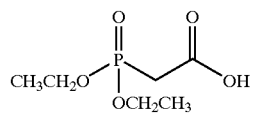 |
| 3-[2-(1,2,3,4-Tetrahydroisoquinolinyl)]-1-propanephosphonic acid | 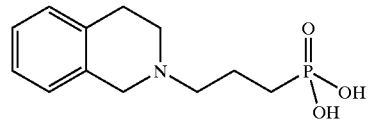 |
| 3-Aminopropylphosphonic acid | $NH_2CH_2CH_2CH_2PO_3H_2$ |
| Propylphosphonic acid | $CH_3CH_2CH_2PO_3H_2$ |
| Ethylphosphonic acid | $CH_3CH_2PO_3H_2$ |
| Methylphosphonic acid | $CH_3PO_3H_2$ |
| tert-Butylphosphonic acid | $(CH_3)_3CPO_3H_2$ |
| Phenylphosphonic acid | 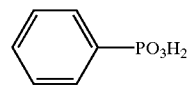 |
| (dl)-2-Amino-3-phosphonopropanoic acid | 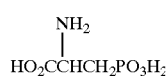 |
| (1-Aminopropyl)phosphonic acid | 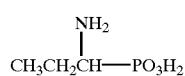 |
| (dl)-2-Amino-5-phosphonopentanoic acid | 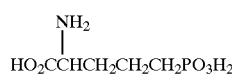 |
| Diethyl phosphoramidate | 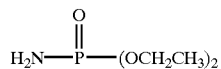 |
| (S)-2-Amino-2-methyl-4-phosphonobutanoic acid | 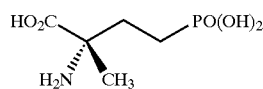 |
| D-(−)-2-Amino-4-phosphonobutanoic acid | 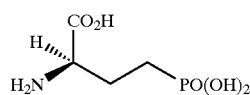 |
| L-(+)-2-Amino-4-phosphonobutanoic acid | 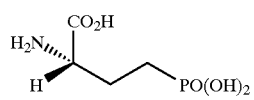 |
| D-(−)-2-Amino-7-phosphonoheptanoic acid | 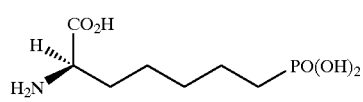 |
| L-(+)-2-Amino-7-phosphonoheptanoic acid | 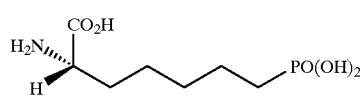 |
| D-(−)-2-Amino-6-phosphonohexanoic acid | 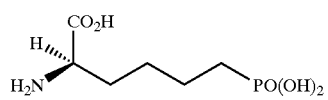 |
| L-(+)-2-Amino-6-phosphonohexanoic acid | 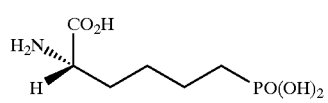 |

TABLE III-continued

| | |
|---|---|
| D-(−)-2-Amino-4-phosphonopentanoic acid | 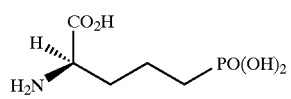 |
| L-(+)-2-Amino-4-phosphonopentanoic acid | 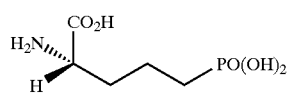 |
| D-(−)-2-Amino-3-phosphonopropanoic acid | 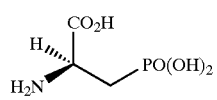 |
| L-(+)-2-Amino-3-phosphonopropanoic acid | 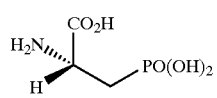 |
| 3-Aminopropyl(methyl)phosphinic acid, hydrochloride | 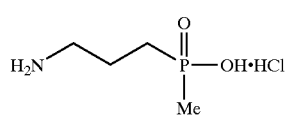 |
| (R)-(−)-3-(2-Carboxypiperazin-4-yl)-propyl-1-phosphonic acid (D-CPP) | 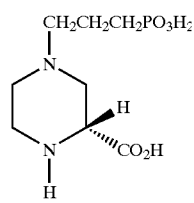 |
| L-4-[Difluoro(phosphono)methyl)]-phenylalanine | 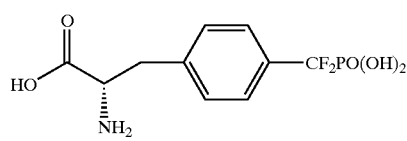 |
| (R,E)-4-(3-Phosphonoprop-2-enyl)piperazine-2-carboxylic acid | 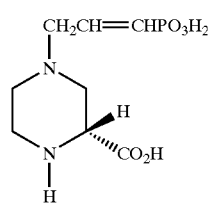 |
| trans-L-4-Phosphonomethylproline, trisodium salt | 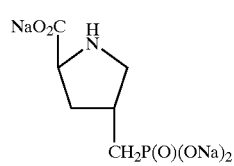 |
| cis-L-4-Phosphonomethylproline, trisodium salt | 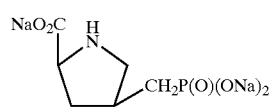 |
| Thiophosphonoformic acid, trisodium salt | 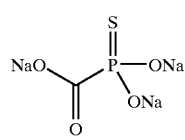 |

TABLE III-continued

| Name | Structure |
|---|---|
| Thiophosphonoacetic acid | HOOC-CH$_2$-P(=S)(OH)$_2$ |
| Thiophosphonoacetic acid, trisodium salt | NaOOC-CH$_2$-P(=S)(ONa)$_2$ |
| Thiophosphonoacetic acid, triethyl ester | EtOOC-CH$_2$-P(=S)(OEt)$_2$ |
| Chloro(thiophosphono)acetic acid, trisodium salt | NaOOC-CHCl-P(=S)(ONa)$_2$ |
| Dichloro(thiophosphono)acetic acid, trisodium salt | NaOOC-CCl$_2$-P(=S)(ONa)$_2$ |
| Thiophosphonomethylthiophosphonic acid, tetrasodium salt | (NaO)$_2$(S=)P-CH$_2$-P(=S)(ONa)$_2$ |
| Phenylthiophosphinomethylthio-phosphonic acid, trisodium salt | Ph(NaO)(S=)P-CH$_2$-P(=S)(ONa)$_2$ |
| Propylthiophosphonic acid | CH$_3$CH$_2$CH$_2$PO$_2$H$_2$ (P=S) |
| Ethylthiophosphonic acid | CH$_3$CH$_2$PO$_2$H$_2$ (P=S) |
| Methylthiophosphonic acid | CH$_3$PO$_2$H$_2$ (P=S) |
| tert-Butylthiophosphonic acid | (CH$_3$)$_3$CPO$_2$H$_2$ (P=S) |
| 3-Thiophosphonopropanoic acid | HO$_2$CCH$_2$CH$_2$PO$_2$H$_2$ (P=S) |
| Phenylthiophosphonic acid | C$_6$H$_5$-PO$_2$H$_2$ (P=S) |
| 3-Aminopropylthiophosphonic acid | NH$_2$CH$_2$CH$_2$CH$_2$P(OH)$_2$ (P=S) |
| (dl)-2-Amino-3-thiophosphonopropanoic acid | HO$_2$CCH(NH$_2$)CH$_2$P(OH)$_2$ (P=S) |

TABLE III-continued

| Name | Structure |
|---|---|
| (1-Aminopropyl)thiophosphonic acid | $CH_3CH_2CH(NH_2)-P(=S)(OH)_2$ |
| (dl)-2-Amino-5-thiophosphonopentanoic acid | $HO_2CCH(NH_2)CH_2CH_2CH_2P(=S)(OH)_2$ |
| (S)-2-Amino-2-methyl-4-thiophosphonobutanoic acid | $HO_2C-C(NH_2)(CH_3)-CH_2CH_2-P(=S)(OH)_2$ |
| D-2-Amino-4-thiophosphonobutanoic acid | D-isomer: $HO_2C-CH(NH_2)-CH_2CH_2-P(=S)(OH)_2$ |
| L-2-Amino-4-thiophosphonobutanoic acid | L-isomer: $HO_2C-CH(NH_2)-CH_2CH_2-P(=S)(OH)_2$ |
| D-2-Amino-7-thiophosphonoheptanoic acid | D-isomer: $HO_2C-CH(NH_2)-(CH_2)_5-P(=S)(OH)_2$ |
| L-2-Amino-7-thiophosphonoheptanoic acid | L-isomer: $HO_2C-CH(NH_2)-(CH_2)_5-P(=S)(OH)_2$ |
| D-2-Amino-6-thiophosphonohexanoic acid | D-isomer: $HO_2C-CH(NH_2)-(CH_2)_4-P(=S)(OH)_2$ |
| L-2-Amino-6-thiophosphonohexanoic acid | L-isomer: $HO_2C-CH(NH_2)-(CH_2)_4-P(=S)(OH)_2$ |
| D-2-Amino-5-thiophosphonopentanoic acid | D-isomer: $HO_2C-CH(NH_2)-(CH_2)_3-P(=S)(OH)_2$ |
| L-2-Amino-5-thiophosphonopentanoic acid | L-isomer: $HO_2C-CH(NH_2)-(CH_2)_3-P(=S)(OH)_2$ |
| D-2-Amino-3-thiophosphonopropanoic acid | D-isomer: $HO_2C-CH(NH_2)-CH_2-P(=S)(OH)_2$ |
| L-2-Amino-3-thiophosphonopropanoic acid | L-isomer: $HO_2C-CH(NH_2)-CH_2-P(=S)(OH)_2$ |
| 3-Aminopropyl(methyl)thiophosphinic acid, hydrochloride | $H_2N-(CH_2)_3-P(=S)(Me)(OH) \cdot HCl$ |

TABLE III-continued

| | |
|---|---|
| (R)-3-(3-Carboxy-1-piperazinyl)-1-propyl-thiophosphonic acid | 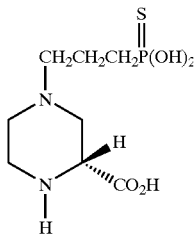 |
| L-4-[Difluoro(thiophosphono)methyl)]-phenylalanine | 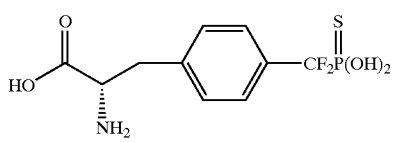 |
| (R,E)-4-(3-Thiophosphonoprop-2-enyl)piperazine-2-carboxylic acid | 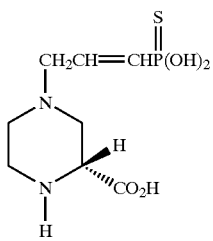 |
| 4-Amino-1-butylphosphonic acid, disodium salt | 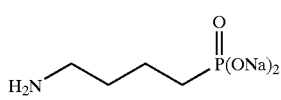 |
| 4-Amino-1-butylthiophosphonic acid, disodium salt | 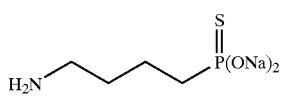 |
| 1-(3-Phosphonopropyl)-benzimidazole, disodium salt | 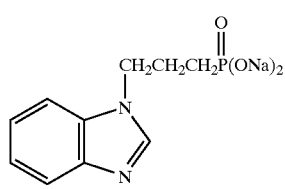 |
| 1-(3-Thiophosphonopropyl)-benzimidazole, disodium salt | 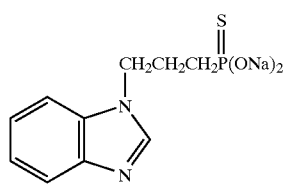 |
| 3-Dimethylamino-1-propylphosphonic acid, disodium salt | 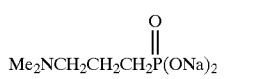 |
| N,N-Diethylphosphonoacetamide, disodium salt | 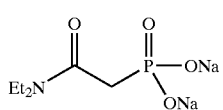 |
| N,N-Diethylthiophosphonoacetamide, disodium salt | 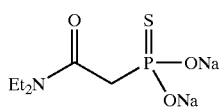 |

TABLE III-continued

| Compound | Structure |
|---|---|
| Diphenylamine-4-phosphonic acid, disodium salt | 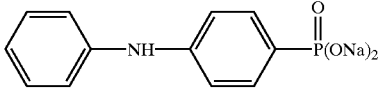 |
| Diphenylamine-4-thiophosphonic acid, disodium salt | 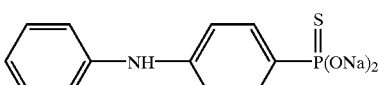 |
| Selenophosphonoformic acid, trisodium salt | 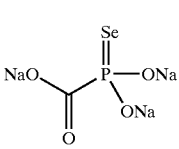 |
| Selenophosphonoacetic acid, trisodium salt | 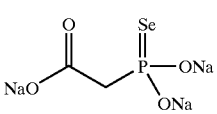 |
| D-2-Amino-3-selenophosphonopropanoic acid | 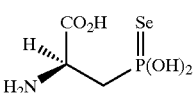 |
| L-2-Amino-3-selenophosphonopropanoic acid | 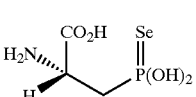 |
| D-2-Amino-4-selenophosphonobutanoic acid | 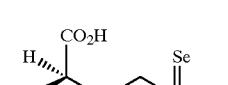 |
| L-2-Amino-4-selenophosphonobutanoic acid | 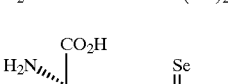 |
| N-Cyclohexylphosphonoacetamide, disodium salt | 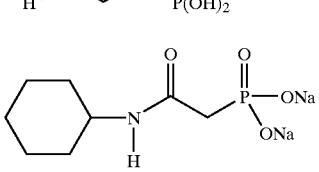 |
| N-Cyclohexylthiophosphonoacetamide, disodium salt | 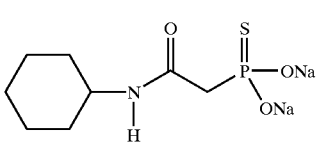 |
| N-Cyclohexylselenophosphonoacetamide, disodium salt | 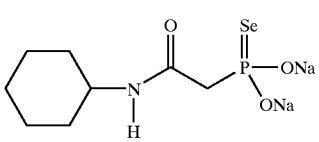 |
| Phosphonoacetic hydrazide, disodium salt | 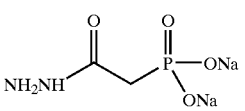 |
| N-Hydroxyphosphonoacetamide, disodium salt | 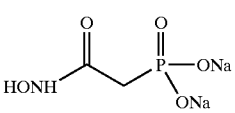 |

TABLE III-continued

| | |
|---|---|
| N-Hydroxythiophosphonoacetamide, disodium salt | 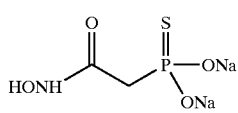 |
| Thiophosphonoacetic hydrazide, disodium salt | 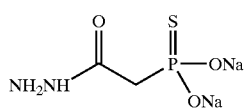 |
| N-Phosphonoacetyl-L-alanine, trisodium salt | 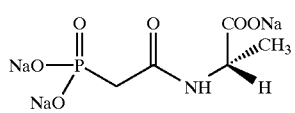 |
| N-Thiophosphonoacetyl-L-alanine, trisodium salt | 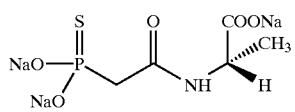 |
| N-Phosphonoacetyl-Glycine, trisodium salt | 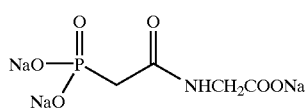 |
| N-Thiophosphonoacetyl-Glycine, trisodium salt | 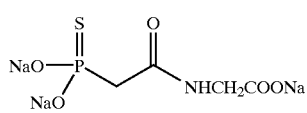 |
| N-(Phosphonoactyl)-L-asparagine-Glycine, tetrasodium salt | 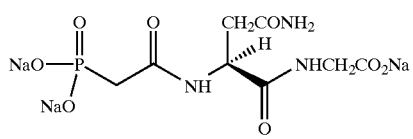 |
| N-(Thiophosphonoactyl)-L-asparagine-Glycine, tetrasodium salt | 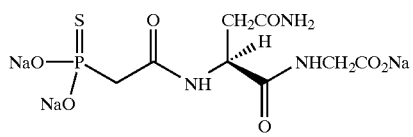 |
| (S)-2-Pyrrolidinemethylthiophosphonic acid, disodium salt | 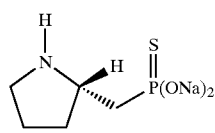 |
| (dl)-3-Amino-butylphosphonic acid, disodium salt | 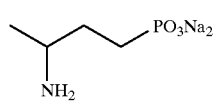 |
| (dl)-3-Amino-pentylphosphonic acid, disodium salt | 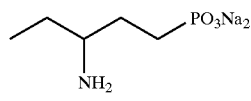 |
| (dl)-3-Amino-hexylphosphonic acid, disodium salt | 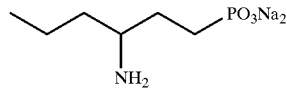 |
| (dl)-3-Amino-heptylphosphonic acid, disodium salt | 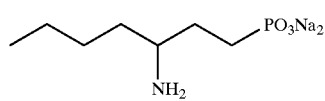 |

TABLE III-continued

| Name | Structure |
|---|---|
| (dl)-3-Amino-octylphophonic acid, disodium salt | CH₃(CH₂)₄CH(NH₂)CH₂CH₂PO₃Na₂ |
| (dl)-3-Amino-4-methyl-pentylphosphonic acid, disodium salt | (CH₃)₂CHCH(NH₂)CH₂CH₂PO₃Na₂ |
| 3-Amino-3-methyl-butylphosphonic acid, disodium salt | (CH₃)₂C(NH₂)CH₂CH₂PO₃H₂ |
| (dl)-3-Amino-3-phenyl-propylphosphonic acid, disodium salt | PhCH(NH₂)CH₂CH₂PO₃Na₂ |
| (dl)-3-Amino-4-phenyl-butylphosphonic acid, disodium salt | PhCH₂CH(NH₂)CH₂CH₂PO₃Na₂ |
| (dl)-3-Amino-4-phenyl-pentylphosphonic acid, disodium salt | PhCH(CH₃)CH(NH₂)CH₂CH₂PO₃Na₂ |
| (dl)-3-Amino-3-phenyl-butylphosphonic acid, disodium salt | PhC(CH₃)(NH₂)CH₂CH₂PO₃Na₂ |
| (dl)-2-Amino-2-(2-phosphonoethyl)-1,2,3,4-tetrahydronaphthalene, disodium salt | 2-amino-2-(2-phosphonoethyl)tetrahydronaphthalene, Na₂ salt |
| 1-Amino-1-(2-phosphonoethyl)-cyclohexane, disodium salt | 1-amino-1-(2-phosphonoethyl)cyclohexane, Na₂ salt |
| (dl)-2-(2-Amino-4-phosphonobutoxy)tetrahydropyran, disodium salt | THP-O-CH₂CH(NH₂)CH₂CH₂PO₃Na₂ |
| (dl)-3-Amino-4-hydroxybutylphosphonic acid, disodium salt | HOCH₂CH(NH₂)CH₂CH₂PO₃Na₂ |
| 3-Phosphonopropanesulfonic acid, trisodium salt | (NaO)₂P(=O)CH₂CH₂CH₂SO₃Na |

TABLE III-continued

| | |
|---|---|
| Pamidronic acid (3-Amino-1-hydroxypropane-1,1-bisphosphonic acid) | 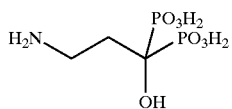 |
| 3-Amino-1-hydroxypropane-1,1-bisphosphonic acid, tetrasodium salt | 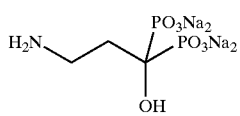 |
| Diethyl 2-pyrrolidinylphosphonate | 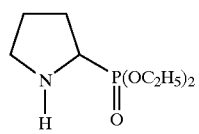 |
| 2-Pyrrolidinylphosphonic acid, disodium salt | 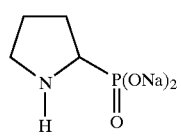 |
| 1,1-Dioxo-2-(3-phosphonopropyl)-isothiazoline, disodium salt | 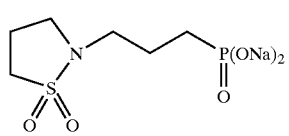 |
| 1,1-Dioxo-2-(3-thiophosphonopropyl)-isothiazolidine, disodium salt | 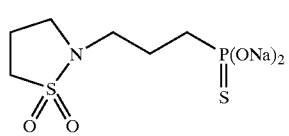 |
| 2-Deoxy-2-phosphonoacetylamino-D-glucose | 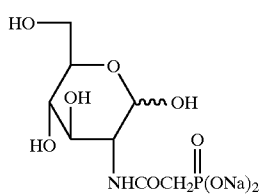 |
| 2-Deoxy-2-thiophosphonoacetylamino-D-glucose | 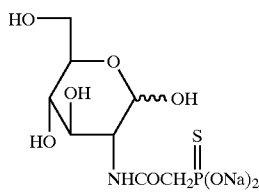 |
| 1-Amino-3-sulfopropane-1,1-bisphosphonic acid | 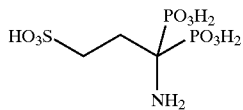 |
| 1-Amino-3-sulfopropane-1,1-bisphosphonic acid, pentasodium salt | 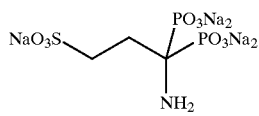 |

TABLE III-continued

| | |
|---|---|
| 3-Hydroxy-3-(2-pyridyl)propenyl-2-phosphonic acid, disodium salt | 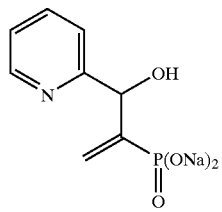 |
| 3-Hydroxy-3-(3-pyridyl)propenyl-2-phosphonic acid, disodium salt | 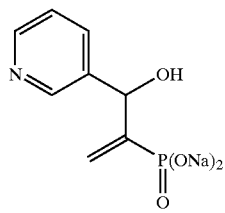 |
| 3-Hydroxy-3-(4-pyridyl)propenyl-2-phosphonic acid, disodium salt | 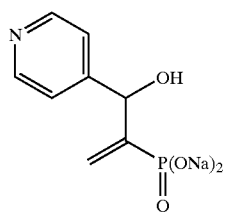 |
| 3-Amino-3-(2-pyridyl)propenyl-2-phosphonic acid, disodium salt | 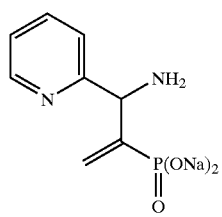 |
| 3-Amino-3-(3-pyridyl)propenyl-2-phosphonic acid, disodium salt | 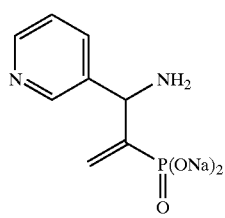 |
| 3-Amino-3-(4-pyridyl)propenyl-2-phosphonic acid, disodium salt | 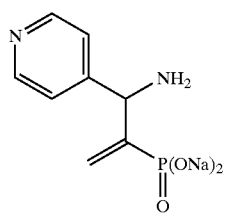 |
| 1,4-Diamino-1-(3-pyridyl)butyl-2-phosphonic acid, disodium salt | 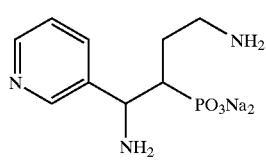 |

TABLE III-continued

| Name | Structure |
|---|---|
| 1,4-Diamino-4-methyl-1-(3-pyridyl)pentyl-2-phosphonic acid, disodium salt | 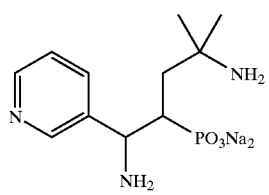 |
| 1,4-Diamino-4-methyl-1-(2-pyridyl)pentyl-2-phosphonic acid, disodium salt | 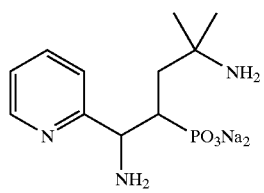 |
| 1,4-Diamino-4-methyl-1-(4-pyridyl)pentyl-2-phosphonic acid, disodium salt | 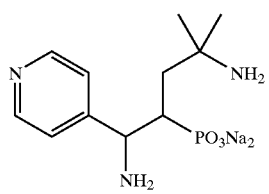 |
| 1,3-Diaminopropane-1,1-bisphosphonic acid, tetrasodium salt | 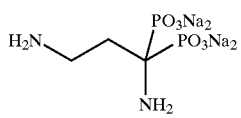 |
| 1-Amino-3-dimethylaminopropane-1,1-bisphosphonic acid, tetrasodium salt | 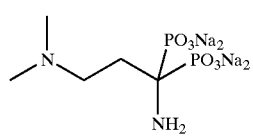 |
| 3-Dimethylamino-1-hydroxypropane-1,1-bisphosphonic acid, tetrasodium salt | 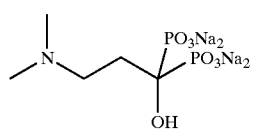 |
| 1-Hydroxy-3-(methylphenylamino)-propane-1,1-bisphosphonic acid, tetrasodium salt | 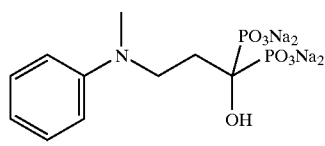 |
| 1-Amino-3-(methylphenylamino)propane-1,1-bisphosphonic acid, tetrasodium salt | 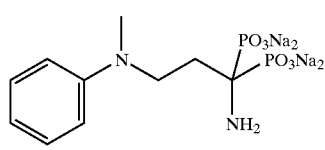 |
| 3-(2-Amino-4,5,7,8-tetrahydro-6H-thiazolo[4,5-d]azepin-6-yl)propyl-phosphonic acid, disodium salt | 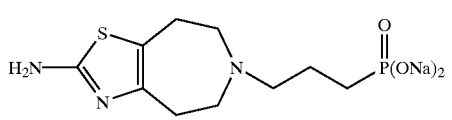 |
| 3-(2-Amino-4,5,7,8-tetrahydro-6H-thiazolo[4,5-d]azepin-6-yl)propyl-thiophosphonic acid, disodium salt | 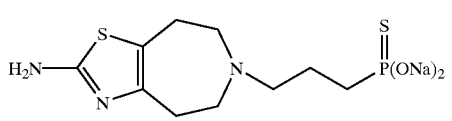 |

TABLE III-continued

| | |
|---|---|
| Ibandronic acid, tetrasodium salt (1-Hydroxy-3-(methylpentylamino)-propane-1,1-bisphosphonic acid, tetrasodium salt) | 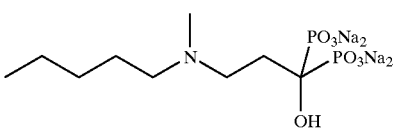 |
| 1-Amino-3-(methylpentylamino)propane-1,1-bisphosphonic acid, tetrasodium salt | 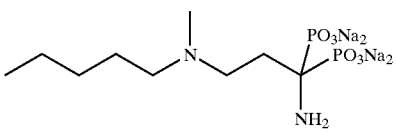 |
| 1-Amino-3-(1-benzimidazolyl)propane-1,1-bisphosphonic acid | 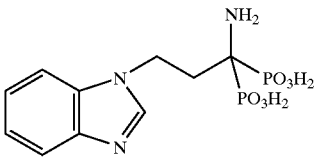 |
| 1-Amino-3-(1-benzimidazolyl)propane-1,1-bisphosphonic acid, tetrasodium salt | 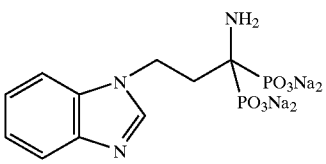 |
| 3-Aminopropane-1,1-bisphosphonic acid, tetrasodium salt | 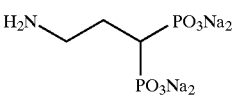 |
| (dl)-3-Aminobutane-1,1-bisphosphonic acid, tetrasodium salt | 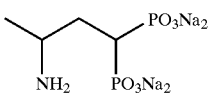 |
| (dl)-3-Aminopentane-1,1-bisphosphonic acid, tetrasodium salt | 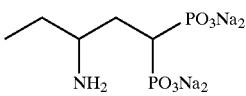 |
| (dl)-3-Aminohexane-1,1-bisphosphonic acid, tetrasodium salt | 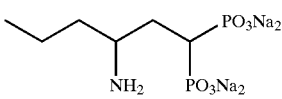 |
| (dl)-3-Aminoheptane-1,1-bisphosphonic acid, tetrasodium salt | 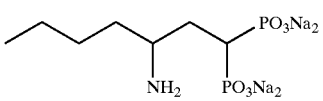 |
| (dl)-3-Aminooctane-1,1-bisphosphonic acid, tetrasodium salt | 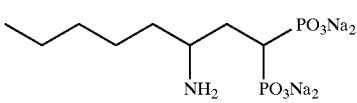 |
| (dl)-3-Amino-4-methylpentane-1,1-bisphosphonic acid, tetrasodium salt | 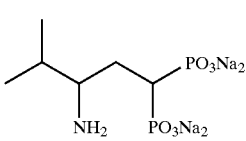 |
| 3-Amino-3-methylbutane-1,1-bisphosphonic acid, tetrasodium salt | 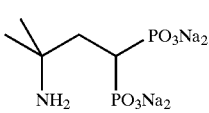 |

TABLE III-continued

| | |
|---|---|
| (dl)-3-Amino-3-phenylpropane-1,1-bisphosphonic acid, tetrasodium salt | 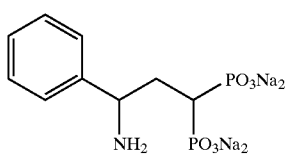 |
| (dl)-3-Amino-4-phenylbutane-1,1-bisphosphonic acid, tetrasodium salt | 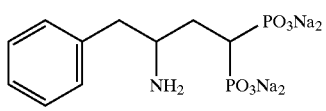 |
| 3-Amino-4-phenylpentane-1,1-bisphosphonic acid, tetrasodium salt | 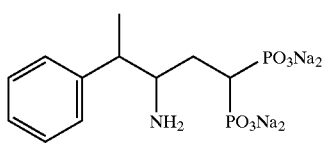 |
| (dl)-3-Amino-3-phenylbutane-1,1-bisphosphonic acid, tetrasodium salt | 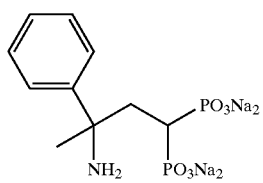 |
| (dl)-2-(2-Amino-1,2,3,4-tetrahydronaphthalenyl)ethane-1,1-bisphosphonic acid, tetrasodium salt | 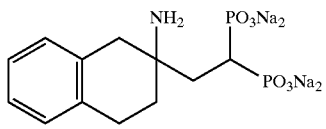 |
| 2-(1-Aminocyclohexyl)ethane-1,1-bisphosphonic acid, tetrasodium salt | 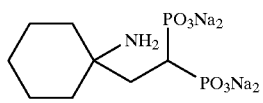 |
| 2-(2-Amino-4,4-bisphosphonobutoxy)-tetrahydropyran, tetrasodium salt | 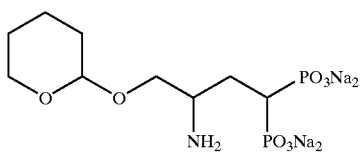 |
| (dl)-3-Amino-4-hydroxybutane-1,1-bisphosphonic acid, tetrasodium salt | 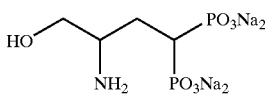 |
| (S)-Hydroxy(2-pyrrolidinyl)methane-bisphosphonic acid, sodium salt | 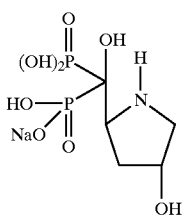 |
| Hydroxy[(2S, 4R)-4-hydroxy-2-pyrrolidinyl]methanebisphosphonic acid tetrasodium salt | 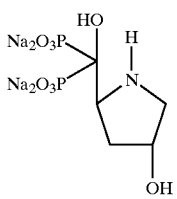 |

TABLE III-continued

| | |
|---|---|
| 2-Amino-1-hydroxyethane-1,1-bisphosphonic acid, tetrasodium salt | 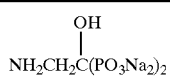 |
| 1,2-Diaminoethane-1,1-bisphonphonic acid, tetrasodium salt | 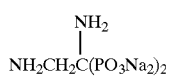 |
| 4-Amino-1-hydroxybutane-1,1-bisphosphonic acid, sodium salt | 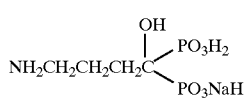 |
| 1,4-Diaminobutane-1,1-bisphosphonic acid, tetrasodium salt |  |
| 5-Amino-1-hydroxypentane-1,1-bisphosphonic acid, tetrasodium salt |  |
| 1,5-Diaminopentane-1,1-bisphosphonic acid, tetrasodium salt |  |
| (S)-2-Amino-1-hydroxypropane-1,1-bisphosphonic acid, tetrasodium salt | 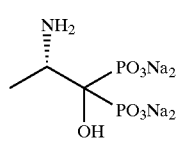 |
| (S)-2-Amino-1-hydroxybutane-1,1-bisphosphonic acid, tetrasodium salt | 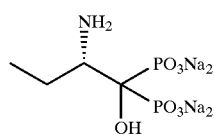 |
| (S)-2-Amino-1-hydroxy-3-methylbutane-1,1-bisphosphonic acid, tetrasodium salt | 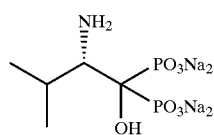 |
| (S)-2-Amino-1-hydroxy-3-phenylpropane-1,1-bisphosphonic acid, tetrasodium salt | 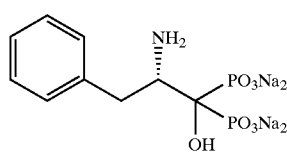 |
| (S)-2-Amino-1,3-dihydroxypropane-1,1-bisphosphonic acid, tetrasodium salt | 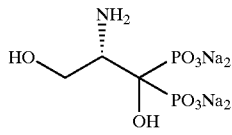 |
| (S)-2,3-Diamino-1-hydroxypropane-1,1-bisphosphonic acid, tetrasodium salt | 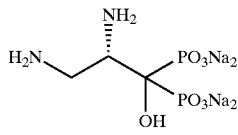 |
| (dl)-3-Amino-1-hydroxy-3-phenylpropane-1,1-bisphosphonic acid, tetrasodium salt | 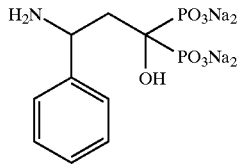 |

TABLE III-continued

| | |
|---|---|
| (S)-3-Amino-2-(4-chlorophenyl)-1-hydroxypropane-1,1-bisphosphonic acid, tetrasodium salt | 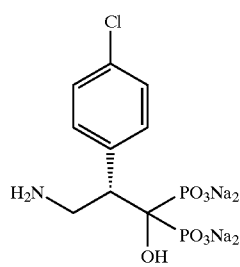 |
| (S)-2-Amino-3-(4-aminophenyl)-1-hydroxypropane-1,1-bisphosphonic acid, tetrasodium salt | 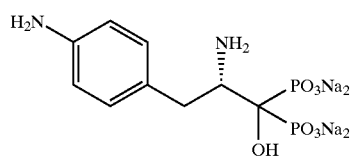 |
| N-Phosphonomethylglycine |  |
| N-Phosphonomethylglycine, trisodium salt |  |
| 2-Phosphonomethylglutaric acid, tetrasodium salt | 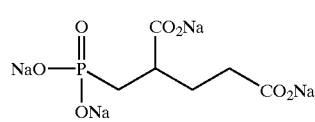 |
| 2-Phosphonomethylsuccinic acid, tetrasodium salt | 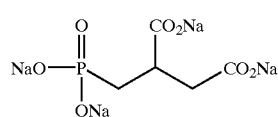 |
| (2R,4S)-4-Phosphonomethylpipecolinic acid, trisodium salt | 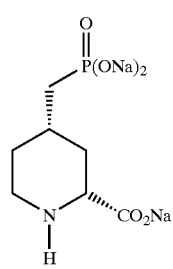 |
| (2R,4S)-4-Phosphonomethylpipecolinamide, disodium salt | 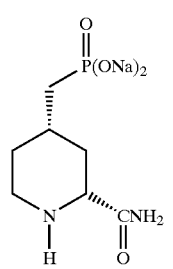 |
| N-Phosphonomethylglycine |  |
| N-Phosphonomethylglycine, trisodium salt |  |

TABLE III-continued

| | |
|---|---|
| 3-[6-Methoxy-2-(1,2,3,4-tetrahydro-isoquinolinyl)]propylphosphonic acid, disodium salt | 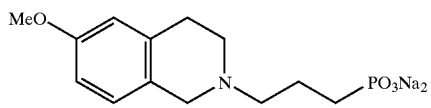 |
| 3-[8-Methoxy-2-(1,2,3,4-tetrahydro-isoquinolinyl)]propylphosphonic acid, disodium salt | 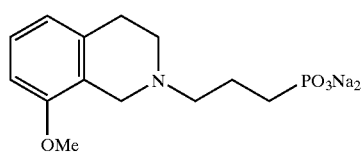 |
| 3-[2-(3-Methoxycarbonyl-1,2,3,4-tetrahydroisoquinolinyl)]-propylphosphonic acid disodium salt | 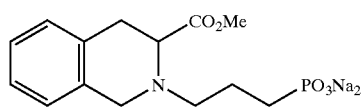 |
| 2-(3-Phosphonopropyl)-1,2,3,4-tetrahydro-9H-pyrido[3,4-b]indole, disodium salt | 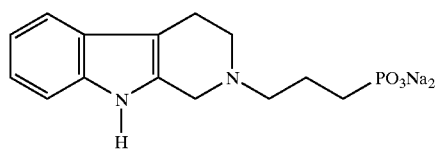 |
| β-D-Glucopyranosylmethylphosphonic acid, disodium salt | 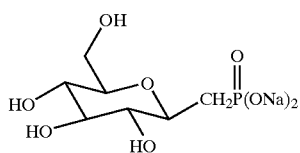 |
| α-D-Glucopyranosylmethylphosphonic acid, disodium salt | 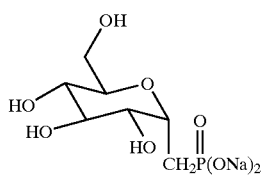 |
| 6-Deoxy-6-C-phosphonomethyl-D-glucono-δ-lactone, disodium salt | 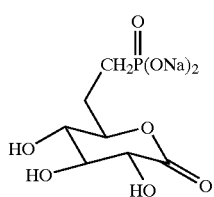 |
| 6-Deoxy-6-C-phosphonomethyl-D-glucose, disodium salt | 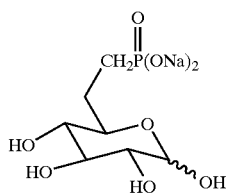 |
| 4-Deoxy-4-C-phosphonomethyl-D-glucose, disodium salt | 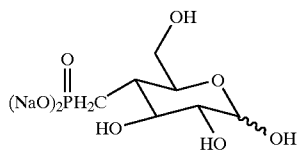 |

TABLE III-continued
| | |
|---|---|
| 3-Deoxy-3-C-phosphonomethyl-D-glucose, disodium salt | 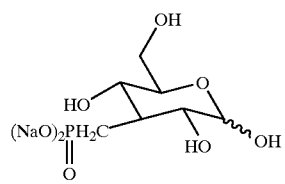 |
| 1-Deoxy-N-phosphonoacetylnojirimycin, disodium salt | 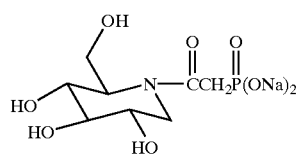 |
| (1,5-Dideoxy-1,5-imino-α-D-glucopyranosyl)methylphosphonic acid, disodium salt | 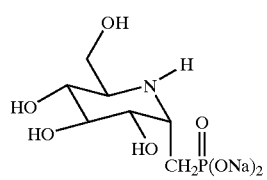 |
| 1,6-Dideoxy-6-C-phosphonomethyl-nojirimycin, disodium salt | 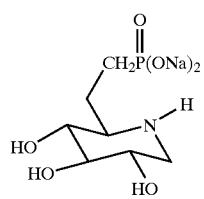 |
TABLE IV
| | |
|---|---|
| $Na^+{}^-O_3SO(CH_2)_5OSO_3{}^-\ Na^+$ | I |
| 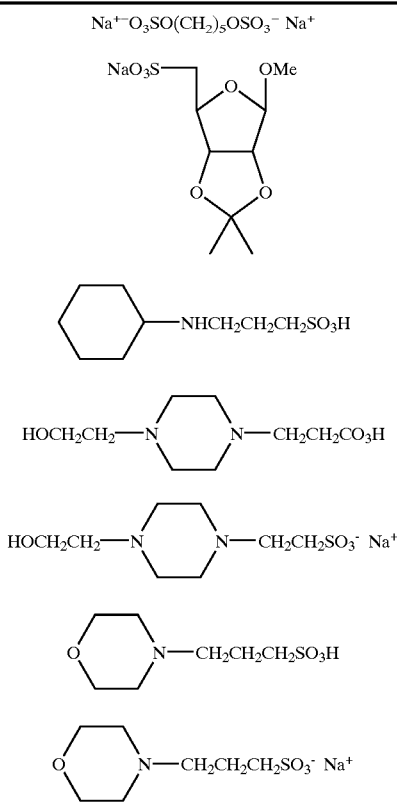 | II–VII |
| $HOCH_2CH_2CH_2CH_2SO_3{}^-\ Na^+$ | VIII |
| $(Na^+{}^-O_3SCH_2CH_2CH_2CH_2)_2O$ | IX |
| 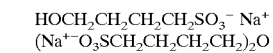 | X |
| 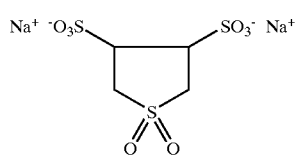 | XI |
| 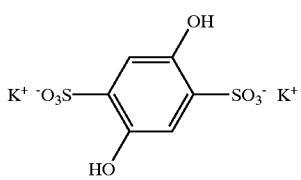 | XII |
| 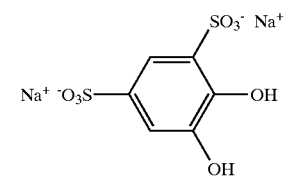 | |
| 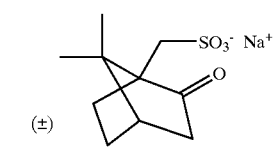 | XIII |

TABLE IV-continued

| | |
|---|---|
| 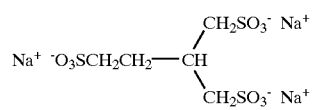 | XIV |
| 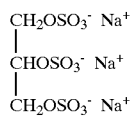 | XV |
| 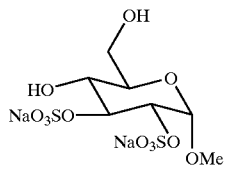 | XVI |
| 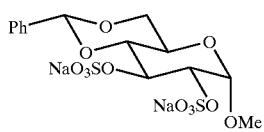 | XVII |
| 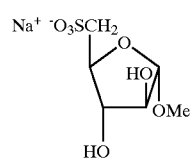 | XVIII |
| 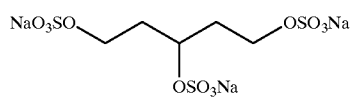 | XIX |
| 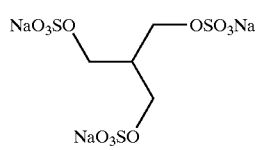 | XX |
| 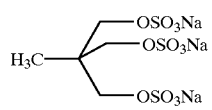 | XXI |
| 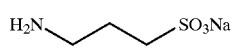 H$_2$N$\diagup\!\diagup\!\diagup$SO$_3$Na | XXII |
| 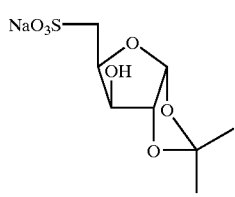 | XXIII |
| 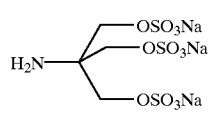 | XXIV |
|  H$_2$N$\diagup\!\diagup$OSO$_3$H | XXV |

TABLE IV-continued

| | |
|---|---|
| 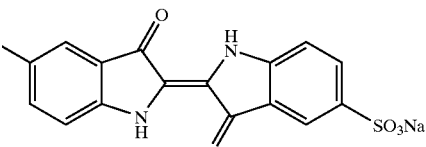 | XXVI |
|  NaO$_3$SNH$\diagup\!\diagup$OSO$_3$Na | XXVII |
| H$_2$N$\diagup\!\diagup\!\diagup$OSO$_3$Na | XXVIII |
| 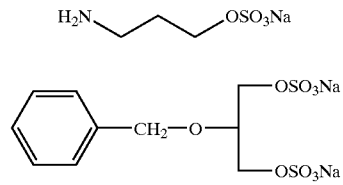 | XXIX |
| NaO$_3$SNH$\diagup\!\diagup\!\diagup$OSO$_3$Na | XXX |
| 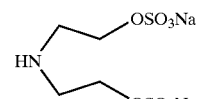 | XXXI |
| 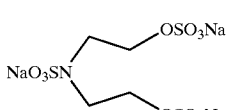 | XXXII |
| 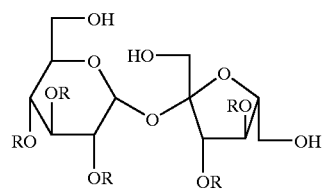
R = SO$_3$Na | XXXIII |
| H$_2$N$\diagup\!\diagup$SO$_3$H | XXXIV |
| NaO$_3$SO$\diagup\!\diagup\!\diagup$SO$_3$Na | XXXV |
| 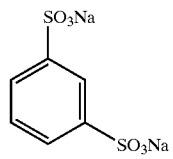 | XXXVI |
| 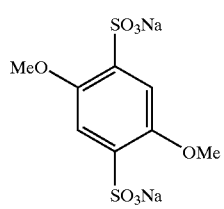 | XXXVII |

TABLE IV-continued

| Structure | Label |
|---|---|
| 2,3-dimethoxybenzene-1,4,5-trisulfonate, trisodium salt | XXXVIII |
| 2,5-dimethoxybenzene-1,4-disulfonate, dipotassium salt | XXXIX |
| 1,3-cyclohexanediol bis(sodium sulfate) | XL |
| bis-benzylidene acetal disulfate (disodium) | XLI |
| polyol monosulfate (sodium) | XLII |
| 1-amino-2-hydroxynaphthalene-4-sulfonic acid | XLIII |
| 1,2-diaminonaphthalene-4-sulfonic acid | XLIV |
| benzyl-protected polyol disulfate (disodium) | XLV |
| heptane-1,3,5,7-tetrayl tetrakis(sodium sulfate) | XLVI |
| CH₃CH₂CH₂CH₂SO₃Na | XLVII |
| CH₃(CH₂)₈CH₂SO₃Na | XLVIII |
| isopropyl sulfonate, sodium salt | XLIX |
| sec-pentyl sulfonate, sodium salt | L |
| polyol trisulfate (trisodium), R = SO₃Na | LI |
| 4-heptyl sulfonate, sodium salt | LII |
| 4-sulfonato-1,7-heptanediol, sodium salt | LIII |
| N-(pyridin-4-yl)-2-sulfoethanamide, sodium salt | LIV |
| 2,1-benzoxathiol-3(1H)-one 1,1-dioxide | LV |
| 1,2-oxathiolane 2,2-dioxide | LVI |

TABLE IV-continued
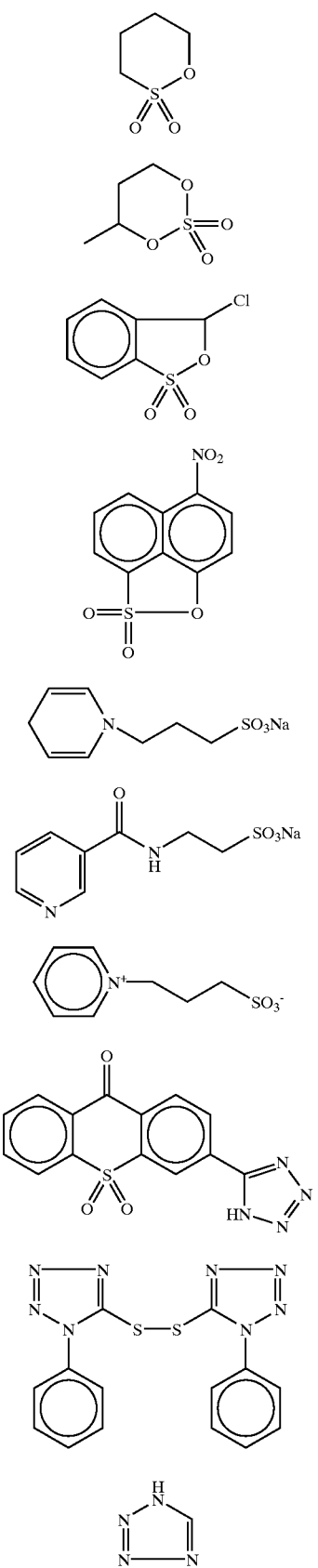
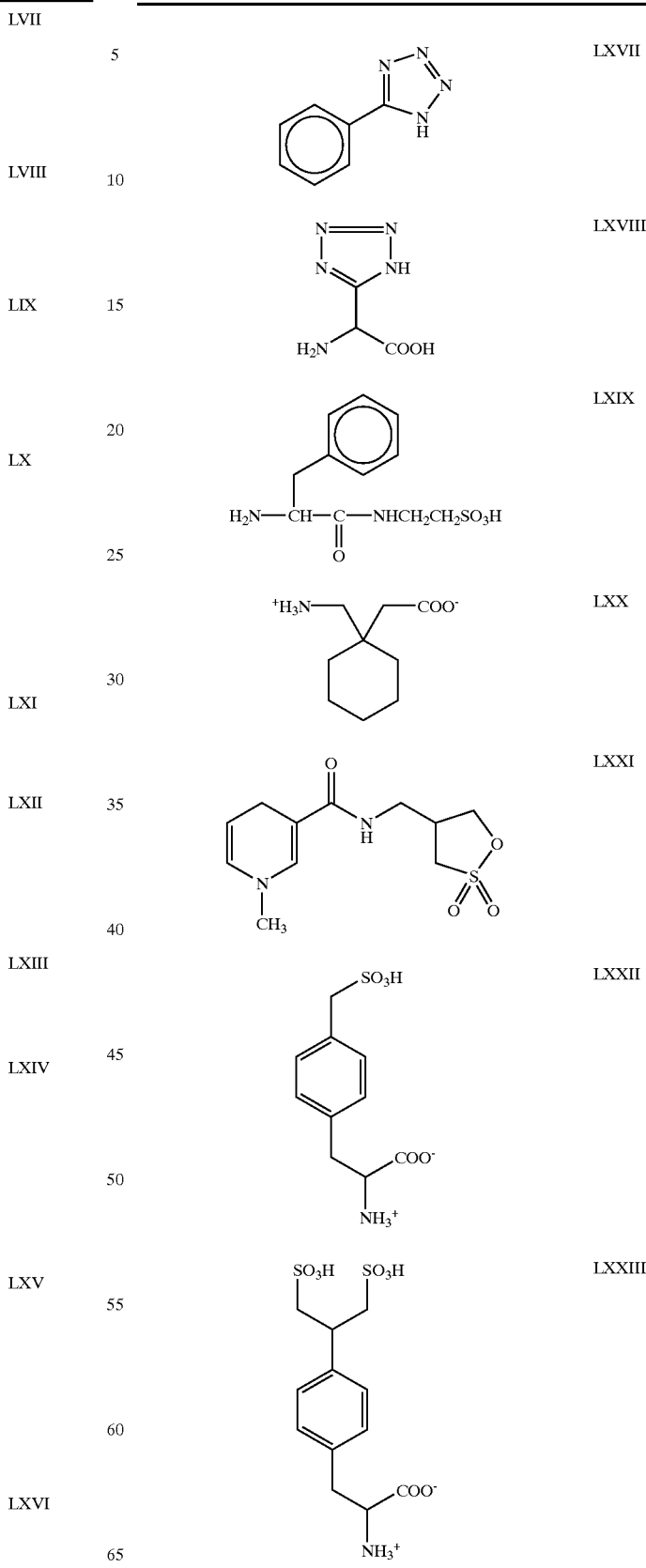

TABLE IV-continued

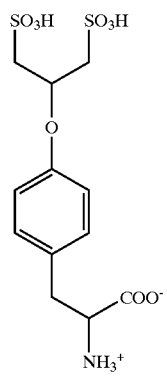

LXXIV

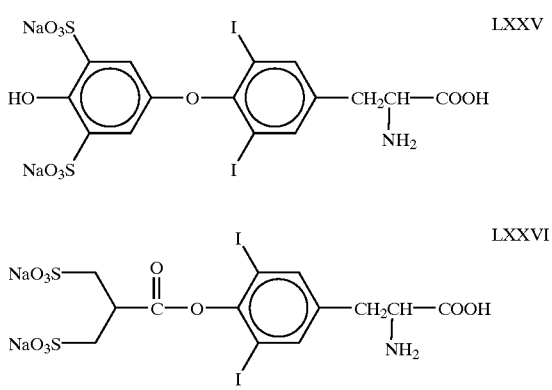

LXXV

LXXVI

TABLE IV-continued

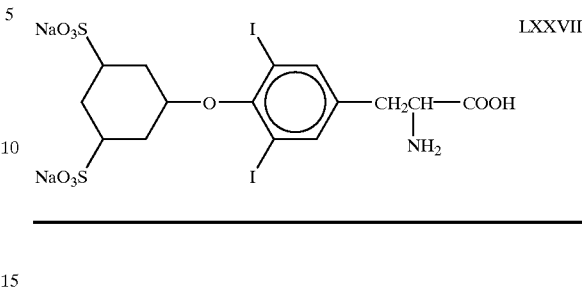

LXXVII

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A method of treating or inhibiting cerebral amyloid angiopathy in a subject, comprising administering an Aβ40 inhibitor to said subject, wherein said Aβ40 inhibitor is 3-amino-1-propanesulfonic acid, or a pharmaceutically acceptable salt thereof.

2. The method of claim 1, wherein said Aβ40 inhibitor is administered in a pharmaceutically acceptable formulation.

3. The method of claim 2, wherein said pharmaceutically acceptable formulation is a dispersion system.

4. The method of claim 2, wherein said pharmaceutically acceptable formulation comprises a lipid-based formulation.

5. The method of claim 2, wherein said pharmaceutically acceptable formulation comprises a liposome formulation.

6. The method of claim 2, wherein said pharmaceutically acceptable formulation comprises a multivesicular liposome formulation.

7. The method of claim 2, wherein said pharmaceutically acceptable formulation comprises a polymeric matrix.

8. The method of claim 7, wherein said polymeric matrix is selected from the group consisting of naturally derived polymers, selected from the group consisting of albumin, alginate, cellulose derivatives, collagen, fibrin, gelatin, and polysaccharides.

9. The method of claim 7, wherein said polymeric matrix is selected from the group consisting of synthetic polymers, polyesters (PLA, PLGA), polyethylene glycol, poloxomers, polyanhydrides, and pluronics.

10. The method of claim 8, wherein said polymeric matrix is in the form of microspheres.

11. The method of claim 2, wherein the pharmaceutically acceptable formulation provides sustained delivery of said Aβ40 inhibitor to a subject.

12. The method of claim 1, comprising administering an Aβ40 inhibitor to said subject in an effective amount and manner such that said Aβ40 inhibitor contacts a blood vessel wall cell in said subject and that cerebral amyloid angiopathy is inhibited.

13. The method of claim 12, wherein said blood vessel wall cell is selected from the group consisting of blood vessel wall smooth muscle cells, pericytes and endothelial cells.

14. The method of claim 12, wherein said blood vessel wall cell is a blood vessel wall smooth muscle cell.

15. The method of claim 12, wherein the death of said blood vessel wall cell is prevented.

16. The method of claim 12, wherein structural changes to said blood vessel wall cell are prevented.

17. A method of diagnosing cerebral amyloid angiopathy in a subject, comprising administering an imageable Aβ40 inhibitor to said subject in such a manner that said imageable Aβ40 inhibitor is allowed to contact cerebral blood vessels which are likely areas for cerebral amyloid angiopathy, and imaging said areas to determine the presence or absence of said imageable Aβ40 inhibitor in said areas such that diagnosis can be made, wherein said Aβ40 inhibitor has the structure:

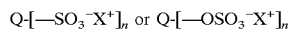

wherein Q is a carrier group; $X^+$ is a cationic group; and n is one.

* * * * *